United States Patent [19]

Corbier et al.

[11] Patent Number: 5,807,878
[45] Date of Patent: Sep. 15, 1998

[54] TETRASUBSTITUTED IMIDAZOLES

[75] Inventors: Alain Corbier, Verrieres-le-Buisson; Pierre Deprez, Thiais; Michel Fortin, Paris; Jacques Guillaume, Livry-Gargan; Bertrand Heckmann, Cachan, all of France

[73] Assignee: Roussel Uclaf, France

[21] Appl. No.: 700,467

[22] PCT Filed: Feb. 27, 1995

[86] PCT No.: PCT/FR95/00227

§ 371 Date: Aug. 30, 1996

§ 102(e) Date: Aug. 30, 1996

[87] PCT Pub. No.: WO95/23791

PCT Pub. Date: Sep. 8, 1995

[30] Foreign Application Priority Data

Mar. 4, 1994 [FR] France .................................. 94 02517

[51] Int. Cl.[6] ...................... A61K 31/415; C07D 233/58; C07D 233/60; C07D 233/84
[52] U.S. Cl. .......................... 514/385; 514/396; 514/399; 548/335.1; 548/326.5; 548/340.1; 548/341.1; 548/342.5; 548/342.1; 548/343.5; 548/346.1
[58] Field of Search ...................... 514/385, 396, 514/399; 548/335.1, 326.5, 340.1, 341.1, 342.5, 342.1, 343.5, 346.1

[56] References Cited

U.S. PATENT DOCUMENTS 5,468,764  11/1995  Heitsch et al. .......................... 514/382

FOREIGN PATENT DOCUMENTS

| 0503162 | 9/1992 | European Pat. Off. . |
| 503162 | 9/1992 | European Pat. Off. . |
| 0560177 | 9/1993 | European Pat. Off. . |
| 560177 | 9/1993 | European Pat. Off. . |
| 0577023 | 1/1994 | European Pat. Off. . |
| 0577025 | 1/1994 | European Pat. Off. . |
| 577023 | 1/1994 | European Pat. Off. . |
| 577025 | 1/1994 | European Pat. Off. . |

OTHER PUBLICATIONS

"Potent Imidazole Angiotensin II Antagonists: Acyl Sulfonamides and Acyl Sulfamides as Tetrazole Replacements," Naylor et al., *Bioorganic & Medicinal Chemistry Letters*, vol. 4, No. 1, pp. 69–74, 1994.

Primary Examiner—Johann Richter
Assistant Examiner—Jane C. Osweeki
Attorney, Agent, or Firm—Bierman, Muserlian and Lucas

[57] ABSTRACT

A compound of the formula

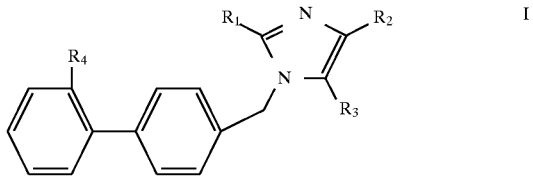

wherein the substituents are defined in the specification useful for the treatment of cardiovascular disorders.

9 Claims, No Drawings

TETRASUBSTITUTED IMIDAZOLES

This application is a 371 of PCT/FR95/00227 filed Feb. 27, 1995.

The present invention relates to new tetrasubstituted derivatives of imidazole, their preparation process, the new intermediates obtained, their use as medicaments and the pharmaceutical compositions containing them.

A subject of the invention is the products of formula (I):

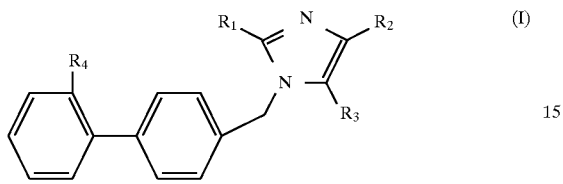

in which $R_1$ represents a linear or branched alkyl, alkylthio and alkoxy radical containing at most 6 carbon atoms, an aryl, arylthio, aryloxy, arylalkyl radical, in which the alkyl radical is linear or branched and contains at most 6 carbon atoms, $R_2$ represents:

a) the —S—R, —O—R and

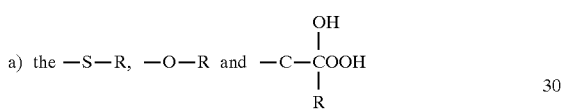

radicals in which R represents a linear or branched alkyl or alkenyl radical containing at most 8 carbon atoms, a cycloalkyl radical containing at most 6 carbon atoms or an aryl radical, the alkyl, alkenyl, cycloalkyl and aryl radicals being optionally substituted by one or more radicals chosen from halogen atoms, the following radicals: hydroxyl, linear or branched alkoxy and alkylthio containing at most 6 carbon atoms and phenyl itself optionally substituted by one or more radicals chosen from halogen atoms, the hydroxyl radical and linear or branched alkoxy radicals containing at most 6 carbon atoms, b) a halogen atom, c) a

radical in which Z represents a hydroxyl, alkoxy or free, salified or esterified carboxy radical.

$R_3$ is chosen from a) the —S—R radical as defined above, b) the

radical in which X represents an oxygen, sulphur atom, an N—O—$R_6$ radical in which $R_6$ represents a hydrogen atom or a linear or branched alkyl radical containing at most 6 carbon atoms, optionally substituted by a free, salified or esterified carboxy radical, or X represents a radical

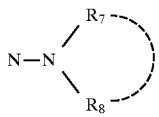

in which $R_7$ and $R_8$, identical or different, represent a hydrogen atom, a linear or branched alkyl radical containing at most 6 carbon atoms, or a phenyl radical, the alkyl and phenyl radicals being optionally substituted by one or more radicals chosen from halogen atoms, the following radicals: hydroxyl, cyano, nitro, alkyl, cycloalkyl and alkoxy, linear or branched containing at most 6 carbon atoms, or $R_7$ and $R_8$ form together with the nitrogen atom to which they are linked a radical chosen from the following radicals: pyrrolyl, pyrrolinyl, pyrrolidinyl, piperazinyl, alkylpiperazinyl, phenylpiperazinyl, piperidyl, morpholinyl and indolinyl, and $R_5$ represents:

i) an optionally substituted cycloalkyl radical or a linear or branched alkyl radical containing at most 8 carbon atoms, the alkyl radical being substituted when X represents an oxygen atom and optionally substituted when X does not represent an oxygen atom, the cycloalkyl and alkyl radicals being if appropriate substituted by one or more radicals chosen from the following radicals: linear or branched alkylthio containing at most 8 carbon atoms, acyl, free, salified or esterified carboxy, halogen atoms, aryl and arylthio, optionally substituted by one or more radicals chosen from halogen atoms, hydroxyl, cyano, nitro, cycloalkyl, alkyl and alkoxy, linear or branched containing at most 6 carbon atoms, ii) the

radical in which $R_9$ represents a hydroxyl, alkoxy, alkylthio radical, an amino radical optionally substituted by a hydroxyl radical or by one or two alkyl radicals, the alkoxy, alkylthio and alkyl radicals being linear or branched containing at most 8 carbon atoms and optionally substituted by one or more radicals chosen from cycloalkyl radicals containing at most 6 carbon atoms and aryl radicals, iii) when X represents an oxygen atom, $R_5$ represents an amino radical optionally substituted by a tetrazolyl, alkylsulphonyl, arylsulphonyl or acyl radical or by one or two identical or different radicals chosen from the following radicals: phenyl, phenylalkyl and alkyl, linear or branched containing at most 6 carbon atoms, alkylsulphonyl, arylsulphonyl, acyl, phenyl, phenylalkyl and alkyl being optionally substituted by one or more radicals chosen from halogen atoms, the following radicals: hydroxyl, cyano, nitro, cycloalkyl, alkyl and alkoxy, linear or branched containing at most 6 carbon atoms, the tetrazolyl radical being optionally substituted by a linear or branched alkyl radical containing at most 6 carbon atoms or a phenyl radical, these alkyl and phenyl radicals being themselves optionally substituted by one or more radicals chosen from halogen atoms, the following radicals: hydroxyl, cyano, nitro, cycloalkyl, alkyl and alkoxy, linear or branched containing at most 6 carbon atoms, iiii) when X represents an oxygen atom, $R_5$ represents a tetrazolyl radical, optionally salified, a thienyl or phenyl, these radicals being optionally substituted by a linear or branched alkyl radical containing at most 6 carbon atoms, iiiii) when X represents an oxygen atom, $R_5$ represents a mercapto radical optionally substituted by a tetrazolyl, phenyl or alkyl radical, the tetrazolyl radical being optionally substituted by an alkyl or phenyl radical, all the alkyl and phenyl radicals being themselves optionally substituted by one or more radicals chosen from halogen atoms, the following radicals: hydroxyl, cyano, nitro, cycloalkyl, alkyl and alkoxy, linear or branched containing at most 6 carbon atoms, c) the

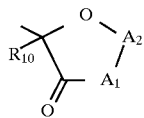

radical, in which $A_1$ represents an oxygen atom or an $N-R_{11}$ radical in which $R_{11}$ represents a phenyl, cycloalkyl, alkyl, aralkyl or cycloalkylalkyl radical, in which radicals the alkyl radicals are linear or branched containing at most 6 carbon atoms and the cycloalkyl radicals contain at most 6 carbon atoms, $A_2$ represents the radical

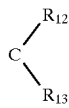

in which $R_{12}$ and $R_{13}$, identical or different are chosen from the hydrogen atom, linear or branched alkyl radicals containing at most 6 carbon atoms and the phenyl radical, the alkyl and phenyl radicals being optionally substituted by one or more halogen atoms, or $R_{12}$ and $R_{13}$ form together an oxo or thioxo radical, $R_{10}$ represents a linear or branched alkyl, alkenyl or alkynyl radical containing at most 6 carbon atoms, a phenyl, benzyl and phenethyl radical, the alkyl radical being optionally substituted by one or more halogen atoms, $R_4$ represents a) the guanidinosulphonyl radical optionally substituted on one or both of the nitrogen atoms by an alkyl, cyano, nitro, alkoxy, phenyl or benzyl radical b) the following radicals: $-(CH_2)_{m1}-COOR_{14}$, $-(CH_2)_{m1}-CONHR_{14}$, $-(CH_2)_{m1}-CN$, in which m1 represents an integer from 0 to 4, $-SO_2-NH-SO_2-R_{14}$, $-NH-SO_2-R_{14}$, $-PO_3R_{14}$, $-NH-SO_2-CF_3$ and

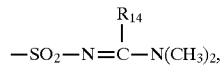

$-(CH_2)_{m1}-SO_3R_{14}$, $-CO-NH-OR_{14}$, $-CO-NH-NH-SO_2-CF_3$, $-CO-NH-SO_2-R_{14}$, $-CH_2SO_2NHCO-R_{14}$, $-CH_2-SO_2-NHR_{14}$, $-CH_2CONH-SO_2R_{14}$, $-NHSO_2NHCO-R_{14}$, $-NHCONHSO_2-R_{14}$, $NH-CH_2-SO_2-NHR_{14}$, $-CONHSO_2NR_{14}R_{15}$, $-SO_2NHCONR_{14}R_{15}$, $-SO_2N(R_{14})OR_{15}$, $-SO_2NHPO(R_{14})_2$, $-CONHPO(R_{14})_2$, $-SO_2NHCN$, $-SO_2NHCOR_{14}$, $SO_2-NHCO_2R_{14}$, $-SO_2NHSO_2NR_{14}R_{15}$, $-SO_2NHSO_2N(-CH_2-CH_2-)_2D$, $-NHSO_2NHSO_2R_{14}$, $-NHSO_2NHPO(R_{14})_2$, $-NR_{14}COCO_2H$, $-SO_2NHCO_2R_{14}$, 13 $SO_2-NH-CS-R_{14}$, $-SO_2-NH-CS-NH-R_{14}$, with D representing an oxygen or sulphur atom, c) the $-SO_2-W-R_{14}$ radical in which W represents the $-NR_{15}-$, $-NH-CO-$, $-NH-CO-O-$, $-N=CH-N-R_{15}-$ or $-NH-CO-NR_{15}-$ radical, in which radicals either $R_{14}$ and $R_{15}$, identical or different, are chosen from the hydrogen atom, the linear or branched alkyl or alkenyl radical containing at most 8 carbon atoms, the cycloalkyl radical containing at most 6 carbon atoms and the aryl radical, the alkyl, alkenyl, cycloalkyl and aryl radicals being optionally substituted by one or more radicals chosen from halogen atoms, the following radicals: hydroxyl, alkoxy containing at most 4 carbon atoms, nitro, cyano, amino, mono and dialkylamino, free, salified or esterified carboxy, haloalkyl, alkylthio, haloalkylthio, haloalkoxy, carbamoyl, acyl, acyloxy, cycloalkyl, cycloalkenyl, aryl, phenylthio, pyridyl, tetrazolyl, thienyl, nitropyridyl, pyrimidyl, diazolyl, piperidinyl, alkylpiperidinyl, thiazolyl, alkylthiazolyl, tetrahydrofuranyl and methyltetrahydrofuranyl optionally substituted by one or more radicals chosen from halogen atoms and the hydroxyl or alkoxy radical containing at most 4 carbon atoms; or $R_{14}$ and $R_{15}$ form with the nitrogen atom to which they are linked a radical chosen from the following radicals: pyrrolyl, pyrrolinyl, pyrrolidinyl, piperazinyl, alkylpiperazinyl, phenylpiperazinyl, morpholinyl and indolinyl, it being understood that the alkyl radicals in the products of formula (I) are optionally interrupted by one or more heteroatoms chosen from oxygen, sulphur and nitrogen atoms and all the sulphur atoms in the products of formula (I) can be optionally oxidized in the form of the sulphone or sulphoxide, said products of formula (I) being in all the possible racemic, enantiomeric and diastereoisomeric isomer forms as well as the addition salts with mineral and organic acids or with mineral and organic bases of said products of formula (I).

In the products of formula (I) and in what follows:

the term linear or branched alkyl radical preferably designates one of the following radicals: methyl, ethyl, propyl, isopropyl, butyl, isobutyl, sec-butyl and tert-butyl but can also represent a pentyl or hexyl radical and particularly isopentyl and isohexyl, the term linear or branched alkenyl radical preferably designates one of the following radicals: vinyl, allyl, 1-propenyl, butenyl and particularly 1-butenyl, or pentenyl, the term linear or branched alkynyl radical preferably designates an ethyny, propargyl, butynyl or pentynyl radical.

Among the alkyl radicals interrupted by one or more heteroatoms, the following radicals can be mentioned for example: methoxymethyl, methoxyethoxymethyl, propylthiopropyl, propyloxypropyl, propylthioethyl, methylthiomethyl, the term halogen atom preferably designates the chlorine atom, but can also represent a fluorine, bromine or iodine atom, the term linear or branched alkoxy radical preferably designates one of the following radicals: methoxy, ethoxy, propoxy or isopropoxy, but can also represent a linear, secondary or tertiary butoxy radical, the term acyl radical preferably designates a radical having 1 to 6 carbon atoms such as for example the formyl, acetyl, propionyl, butyryl or benzoyl radical, but also the pentanoyl, hexanoyl, acryloyl, crotonoyl or carbamoyl radical, the term acyloxy radical designates for example a radical in which the acyl radical has the values indicated above and preferably designates a formyloxy, acetyloxy, propionyloxy, butyryloxy or benzoyloxy radical, the term cycloalkyl radical preferably designates the cyclopropyl, cyclobutyl radicals and quite particularly the cyclopentyl and cyclohexyl radicals, the term aryl radical designates the carbocyclic or heterocyclic unsaturated, monocyclic radicals or radicals constituted by condensed rings, it being understood that the heterocyclic radicals can contain one or more identical or different heteroatoms chosen from oxygen, nitrogen or sulphur atoms.

As examples of such an aryl radical, the following radicals can be mentioned: phenyl, naphthyl, thienyl such as 2-thienyl and 3-thienyl, furyl such as 2-furyl, pyridyl such as 2-pyridyl and 3-pyridyl, pyrimidyl, pyrrolyl, thiazolyl, isothiazolyl, pyrazolyl, triazolyl, tetrazolyl, salified tetrazolyl, thiadiazolyl, thiatriazolyl, oxazolyl, oxadiazolyl, 3-or 4-isoxazolyl, benzothienyl such as 3-benzothienyl, benzofuryl, benzopyrrolyl, benzimidazolyl, benzoxazolyl, thionaphthyl, indolyl or purinyl, pyrrolidinyl, piperidino, morpholino, piperazinyl, these radicals being able to be substituted by one or more radicals as defined above such as for example in methylpiperazinyl, fluoromethylpiperazinyl, ethylpiperazinyl, propylpiperazinyl, phenylpiperazinyl or benzylpiperazinyl;

the term arylalkyl designates radicals in which the alkyl and aryl radicals respectively can take the values defined above for these radicals; as examples of such arylalkyl radicals the following radicals can be mentioned: benzyl, diphenylmethyl, triphenylmethyl, naphthylmethyl, indenylmethyl, thienylmethyl such as 2-thienylmethyl, furylmethyl such as furfuryl, pyridylmethyl, pyrimidylmethyl or pyrrolylmethyl, it being understood that in the non-exhaustive list of examples of radicals as mentioned above, the alkyl radical can be represented just as well by ethyl, propyl or butyl radicals such as, for example, in the phenylethyl radical;

the term haloalkyl radical preferably designates the radicals in which the alkyl radical is as defined above and is substituted by one or more halogen atoms as defined above such as for example in bromoethyl, trifluoromethyl, trifluoroethyl or also pentafluoroethyl, the term alkylthio radical preferably designates the radicals in which the alkyl radical is as defined above such as for example in methylthio or ethylthio, the term haloalkylthio radical preferably designates the radicals in which the alkyl radical is as defined above and is substituted by one or more halogen atoms as defined above such as for example in bromoethylthio, trifluoromethylthio, trifluoroethylthio or also pentafluoroethylthio, the term haloalkoxy radical preferably designates the radicals in which the alkoxy radical is as defined above and is substituted by one or more halogen atoms as defined above such as for example in bromoethoxy, trifluoromethoxy, trifluoroethoxy or also pentafluoroethoxy, the term aryloxy radical preferably designates the radicals in which the aryl radical is as defined above such as for example in phenoxy, the term arylthio radical preferably designates the radicals in which the aryl radical represents the radicals as defined above such as for example in phenylthio, the term aryl radical substituted by an alkylthio radical represents for example the benzylthio or phenethylthio radical.

In all the radicals which can be represented by $R_1$, $R_2$, $R_3$ and $R_4$, as defined above, the sulphur atoms can be non-oxidized as in the alkylthio, arylthio, cycloalkylthio radicals such as for example cyclohexylthio or on the contrary be oxidized to give the alkylsulphinyl, cycloalkylsulphinyl, arylsulphinyl, alkylsulphonyl, cycloalkylsulphonyl or arylsulphonyl radicals:

the terms alkylthio, alkylsulphinyl and alkylsulfonyl radicals designate the radicals in which the linear or branched alkyl radical can represent, for example, the values indicted above for the alkyl radical; these radicals therefore preferably represent the following radicals: methylthio, hydroxymethylthio, ethylthio, aminoethylthio, methylsulphinyl, ethylsulphinyl, methylsulphonyl, ethylsulphonyl but can also represent a propylthio, isopropylthio, butylthio, sec-butylthio, tert-butylthio, isopentylthio or isohexylthio radical or those radicals in which the thio radical is oxidized into a sulphinyl or sulphonyl radical, the term arylthio, arylsulphinyl and arylsulphonyl radical designates the radicals in which the aryl radical can represent, for example, the values indicated above for the aryl radical such as, for example, in phenylthio, pyridylthio or pyrimidylthio, imidazolylthio, N-methylimidazolylthio or those radicals in which the thio radical is oxidized into a sulphinyl or sulphonyl radical such as for example in phenylsulphinyl or phenylsulphonyl.

Among the substituents of the optionally oxidized alkylthio, alkoxy, arylthio and aryloxy radicals, the following radicals can be mentioned for example: hydroxyl, alkoxy, free, salified or esterified carboxy, acyl, acyloxy, alkyl, phenyl, halogen atoms.

As examples of alkyl radicals substituted by an aryl radical, there can mentioned, for example, the following radicals: benzyl, diphenylmethyl, triphenylmethyl, naphthylmethyl, indenylmethyl, thienylmethyl such as 2-thienyl methyl, furylmethyl such as furfuryl, pyridylmethyl, pyrimidylmethyl or pyrrolylmethyl, it being understood that in the non-exhaustive list of examples of radicals as mentioned above, the alkyl radical can be just as well represented by ethyl, propyl or butyl radicals such as, for example, in the phenethyl radical.

As examples of alkenyl radicals substituted by an aryl radical, there can be mentioned, for example, the examples given above of arylalkyl radicals in which the alkyl radical is replaced by an alkenyl radical such as for example in the phenylvinyl or phenylallyl radicals, it being understood that in these radicals the phenyl radical can be just as well replaced by a naphthyl, pyridyl radical or also for example one of the aryl radicals as defined above.

The arylalkyl radicals as defined above, preferably designate the alkylphenyl radicals such as benzyl, phenethyl, and also phenylpropyl and phenylbutyl radicals.

The carbamoyl and amino radicals which can be represented by or carried by one or more of the optional substituents of the radicals defined in the products of formula (I) and in what follows, designate radicals in which two identical or different radicals are linked to the nitrogen atom, chosen from the hydrogen atom to produce the amino radical; the alkyl radicals as defined above to produce the monoalkyl- or dialkylamino radicals in which the linear or branched alkyl radicals contain 1 to 6 carbon atoms, all these radicals being optionally substituted as indicated above and hereafter.

When $R_7$ and $R_8$ or $R_{14}$ and $R_{15}$ as defined above, form a heterocycle together with the nitrogen atom to which they are linked, they can be optionally substituted by the substituents already mentioned previously and in particular by one or more radicals chosen from chlorine and fluorine atoms, the following radicals: methyl, ethyl, isopropyl, tert-butyl, methoxy, ethoxy, propoxy, benzoyl, methoxycarbonyl, ethoxycarbonyl, such as for example in methylpiperazinyl, ethylpiperazinyl, propylpiperazinyl, phenylpiperazinyl or benzylpiperazinyl: in these last two radicals, the phenyl and benzyl radicals can be substituted as indicated previously in the aryl, arylalkyl and arylalkenyl radicals, such as for example in chlorophenyl or trifluorophenyl.

The heterocycle which can be formed by $R_7$ and $R_8$ on the one hand, or $R_{14}$ and $R_{15}$ on the other hand, respectively with the nitrogen atom to which they are linked, preferably represents a saturated heterocycle.

Moreover, in the products of formula (I), the carbamoyl or amino radicals are such that the identical or different radicals carried by the nitrogen atom can represent aliphatic or cyclized chains or can form a heterocycle with the nitrogen atom to which they are linked, as has been defined above for $R_7$, $R_8$, $R_{14}$ and $R_{15}$.

The substituted carbamoyl and substituted amino radicals designate respectively the radicals in which the nitrogen atom can be substituted by one or two radicals chosen from the radicals as defined previously in particular the alkyl radical or radicals chosen from the alkyl radicals as defined above such as for example for monoalkylamino in methylamino, ethylamino or isopropylamino or for example for dialkylamino in dimethylamino, diethylamino or also methylthylamino, these alkyl radicals being optionally substituted as is indicated above, such as for example the methoxymethyl, methoxyethyl, ethoxyethyl radicals.

As an example and in a non-exhaustive manner, the term carbamoyl radical designates the carbamoyl radicals substituted on the nitrogen atom by one or two alkyl radicals optionally substituted as defined above, to form in particular an N-monoalkyl carbamoyl group such as N-methylcarbamoyl, N-ethylcarbamoyl or an N,N-dialkyl carbamoyl group, such as N,N-dimethylcarbamoyl, N,N-diethylcarbamoyl; an N-(hydroxyalkyl) carbamoyl group, such as N-(hydroxymethyl) carbamoyl, N-(hydroxyethyl) carbamoyl, phenylcarbamoyl; pyridylcarbamoyl; benzylcarbamoyl; N-methyl N-phenylcarbamoyl; pyridylmethylcarbamoyl. Furthermore, among the substituted alkyl radicals, there can also be mentioned the alkyl radicals substituted by a carbamoyl radical as defined above, to form a carbamoylalkyl group such as carbamoylmethyl or carbamoylethyl.

The amino radical can be an alkoxycarbonylamino radical, this radical then preferably being the tert-butyloxycarbonylamino radical or the benzyloxycarbonylamino radical.

The amino and carbamoyl radicals can also in particular be substituted by one or two amino acids chosen from the 20 natural amino acids such as in particular proline or for example glycine, alanine, leucine, isoleucine, valine or phenylalanine or one of the other natural amino acids known to a man skilled in the art.

According to whether m1 represents the value 0, 1, 2, 3 or 4, the —$(CH_2)_{m1}$— radical represents a single bond, the methylene radical, the ethylene, propylene, isopropylene or butylene radical.

The carboxy radical or radicals of the products of formula (I) can be salified or esterified by the various groups known to a man skilled in the art among which there can be mentioned, for example:

among the salification compounds, mineral bases such as, for example, an equivalent of sodium, potassium, lithium, calcium, magnesium or ammonium or organic bases such as, for example, methylamine, propylamine, trimethylamine, diethylamine, triethylamine, N,N-dimethylthanolamine, tris(hydroxymethyl) amino methane, ethanolamine, pyridine, picoline, dicyclohexylamine, morpholine, benzylamine, procaine, lysine, arginine, histidine, N-methyl-glucamine, among the esterification compounds, the alkyl radicals in order to form alkoxy carbonyl groups such as, for example, methoxycarbonyl, ethoxycarbonyl, tert-butoxycarbonyl or benzyloxycarbonyl, these alkyl radicals being able to be substituted by radicals chosen for example from halogen atoms, the following radicals: hydroxyl, alkoxy, acyl, acyloxy, alkylthio, amino or aryl such as, for example, in the chloromethyl, hydroxypropyl, methoxymethyl, propionyloxymethyl, methylthiomethyl, dimethylaminoethyl, benzyl or phenethyl groups.

The addition salts with mineral or organic acids of the products of formula (I) can be, for example, the salts formed with the following acids: hydrochloric, hydrobromic, hydroiodic, nitric, sulphuric, phosphoric, propionic, acetic, formic, benzoic, maleic, fumaric, succinic, tartaric, citric, oxalic, glyoxylic, aspartic, ascorbic, alkylmonosulphonic such as for example methanesulphonic, ethanesulphonic, propanesulphonic, alkyldisulphonic such as for example methanedisulphonic, alpha, beta-ethanedisulphonic, aryl-monosulphonic such as benzenesulphonic and aryldisulphonic.

When $R_2$ and $R_3$ both represent a sulphurous group, $R_2$ and $R_3$ being identical or different, in the preferred products of the invention, these sulphurous groups do not necessarily have the same oxidation number.

Thus $R_2$ and $R_3$ can in particular represent alkylthio radicals, optionally substituted by one or more halogen atoms such as chlorine and fluorine, to give for example the radicals: —S—$CF_3$; —S—$CHF_2$; —S—$CH_2F$; —S—$CF_2$—$CHF_2$; —S—$CF_2$—$CF_3$.

A particular subject of the invention is the products of formula (I) as defined above and corresponding to formula ($I_A$):

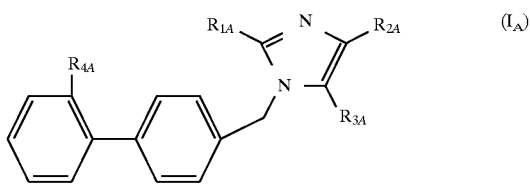

in which $R_{1A}$ represents a linear or branched alkyl or alkylthio radical, containing at most 6 carbon atoms, $R_{2A}$ represents a) the —S—$R_A$ and

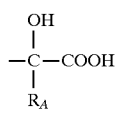

radicals in which $R_A$ represents a linear or branched alkyl or alkenyl radical containing at most 8 carbon atoms, a cycloalkyl or phenyl radical, these radicals being optionally substituted by one or more radicals chosen from halogen atoms and more particularly fluorine, b) a halogen atom, c) a

radical in which Z represents a free, salified or esterified carboxy radical.

$R_{3A}$ represents a) the S—$R_A$ radical as defined above, b) the

radical in which $X_A$ represents an oxygen or sulphur atom, an N—O—$R_6$ radical in which $R_6$ represents a hydrogen atom or a linear or branched alkyl radical containing at most 6 carbon atoms, optionally substituted by a free, salified or esterified carboxy radical or $X_A$ represents an

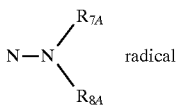

in which $R_{7A}$ and $R_{8A}$, identical or different, represent a hydrogen atom, a linear or branched alkyl radical containing at most 6 carbon atoms, or a phenyl radical, the alkyl and phenyl radicals being optionally substituted by one or more radicals chosen from halogen atoms, the hydroxyl, cyano, nitro radical, linear or branched alkyl, cycloalkyl and alkoxy radicals containing at most 6 carbon atoms, and $R_{5A}$ represents i) a linear or branched alkyl radical containing at most 8 carbon atoms, substituted by one or more radicals chosen from linear or branched alkylthio, alkylsulphone, alkylsulphoxide radicals containing at most 8 carbon atoms, acyl, free, salified or esterified carboxy radicals, halogen atoms, the phenyl and phenylthio radicals optionally substituted by one or more radicals chosen from halogen atoms, the hydroxyl, cyano, nitro radical, linear or branched cycloalkyl, alkyl and alkoxy radicals, containing at most 6 carbon atoms, ii) the

radical in which $Y_3$ represents an optionally salified hydroxyl radical, alkoxy or alkylthio radicals linear or branched containing at most 6 carbon atoms, iii) when $X_A$ represents an oxygen atom, $R_{5A}$ represents an amino radical optionally substituted by an optionally salified tetrazolyl radical or by one or two linear or branched alkyl radicals containing at most 6 carbon atoms, themselves optionally substituted by one or more phenyl or cyclohexyl radicals, iiii) when $X_A$ represents an oxygen atom, $R_{5A}$ represents an optionally salified terazolyl, thienyl or phenyl radical, these radicals being optionally substituted by a linear or branched alkyl radical containing at most 6 carbon atoms, c) the radical

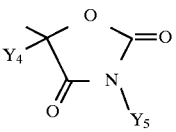

in which $Y_4$ and $Y_5$, identical or different, represent a linear or branched alkyl radical containing at most 6 carbon atoms, $R_{4A}$ represents $SO_2$—$W_A$—$R_{16A}$, in which $W_A$ represents the —NH—, NH—CO—, —NH—CO—O—, N=CH—N—$R_{17A}$ or —NH—CO—NH— radical and $R_{16A}$ and $R_{17A}$ represent a linear or branched alkyl or alkenyl radical containing at most 4 carbon atoms, or an aryl radical, these radicals being optionally substituted by one or more radicals chosen from halogen atoms, the following radicals: hydroxyl, alkoxy containing at most 4 carbon atoms, nitro, cyano, amino, mono- and dialkylamino, free, salified or esterified carboxy, cyclohexyl, cyclohexenyl, pyridyl, thienyl and phenyl, these radicals being optionally substituted by a halogen atom or a hydroxyl or alkoxy radical containing at most 4 carbon atoms, it being understood that the sulphur atoms in the products of formula ($I_A$) can be optionally oxidized in the form of the sulphone or sulphoxide, said products of formula ($I_A$) being in all the possible racemic, enantiomeric and diastereoisomeric isomer forms as well as the addition salts with mineral and organic acids or with mineral and organic bases of said products of formula ($I_A$).

A more particular subject of the invention is the products of formulae (I) and ($I_A$) as defined above and corresponding to formula ($I_B$):

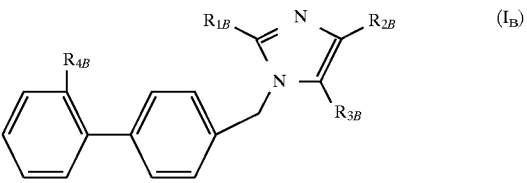

in which $R_{1B}$ represents a linear or branched alkyl or alkylthio radical containing at most 4 carbon atoms, $R_{2B}$ represents a linear or branched alkylthio radical containing at most 4 carbon atoms, a halogen atom or a

radical in which Z represents a free, salified or esterified carboxy radical, $R_{3B}$ represents
a) a linear or branched alkylthio radical containing at most 4 carbon atoms,
b) the

radical in which
$X_B$ represents an oxygen atom or an

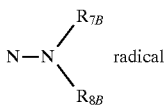

in which $R_{7B}$ and $R_{8B}$, identical or different, represent a hydrogen atom, a linear or branched alkyl radical containing at most 6 carbon atoms, or a phenyl radical, the alkyl and phenyl radicals being optionally substituted by one or more radicals chosen from halogen atoms, the hydroxyl, cyano, nitro and methoxy radical, and $R_{5B}$ represents
i) the —$CHY_1Y_2$ radical in which
$Y_1$ represents a hydrogen or halogen atom, a linear or branched alkyl radical containing at most 8 carbon atoms, phenyl, benzyl and phenethyl radicals, these radicals being optionally substituted by one or more radicals chosen from halogen atoms, the following radicals: hydroxyl, cyano, nitro, linear or branched cycloalkyl, alkyl and alkoxy containing at most 6 carbon atoms, and $Y_2$ represents a free, salified, amidified or esterified carboxy radical and linear or branched acyl, alkylthio, alkylsulphone, alkylsulphoxide radicals, containing at most 6 carbon atoms, phenylthio, phenylsulphone and phenylsulphoxide radicals, all these radicals being optionally substituted by one or more radicals chosen from halogen atoms, the following radicals: hydroxyl, cyano, nitro, linear or branched cycloalkyl, alkyl and alkoxy containing at most 6 carbon atoms,
ii) the

radical in which $Y_3$ represents an optionally salified hydroxyl radical, a linear or branched alkoxy, alkylthio radical containing at most 6 carbon atoms,
iii) when $X_B$ represents an oxygen atom, $R_{5B}$ represents an amino radical optionally substituted by an optionally salified tetrazolyl radical or by one or two linear or branched alkyl radicals containing at most 6 carbon atoms, themselves optionally substituted by one or more phenyl or cyclohexyl radicals,
iiii) when $X_B$ represents an oxygen atom, $R_{5B}$ represents an optionally salified tetrazolyl radical, c) the radical

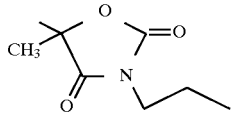

$R_{4B}$ represents the following radicals: —$SO_2$—$NH_2$, —$SO_2$—N=CH—N(CH$_3$)$_2$, $SO_2$—NH—CO—CF$_3$, $SO_2-NH-\underset{\underset{O}{\|}}{C}-V-V_4,$

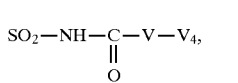

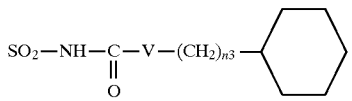

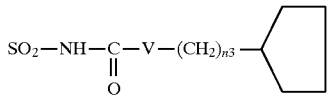

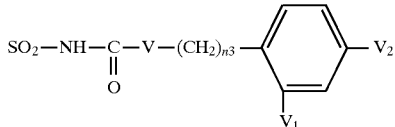

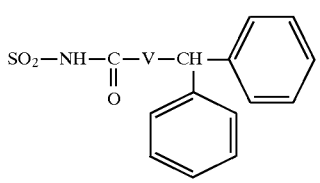

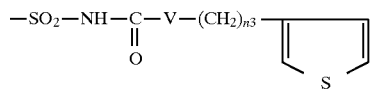

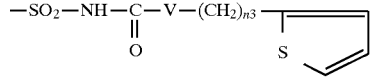

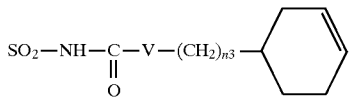

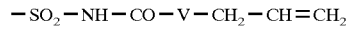

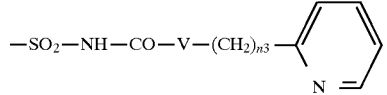

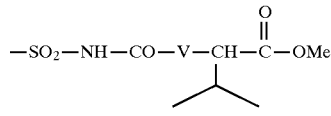

with n3 representing an integer from 0 to 3, V representing —NH—, —O— or a single bond, $V_1$ and $V_2$ identical or different representing a hydrogen atom, a halogen atom in particular chlorine and fluorine and an alkoxy radical in particular methoxy, $V_4$ representing a hydrogen atom, an alkyl radical such as in particular methyl, ethyl, propyl and butyl, it being understood that the sulphur atoms in the products of formula ($I_B$) can be optionally oxidized in the form of the sulphone or sulphoxide, said products of formula ($I_B$) being in all the possible racemic, enantiomeric and diastereoisomeric isomer forms as well as the addition salts with mineral and organic acids or with mineral and organic bases of said products of formula ($I_B$).

Among the values that $R_{4B}$ as defined above can take, there can be mentioned, for example, quite particularly and in a non-exhaustive manner the following radicals:

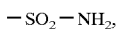
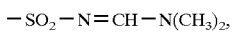
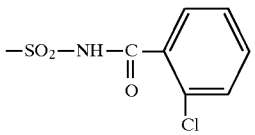
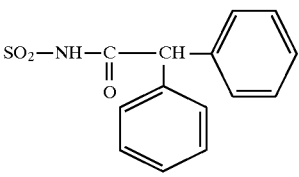
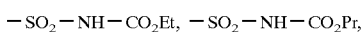
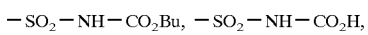
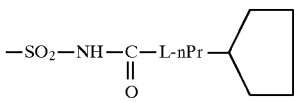
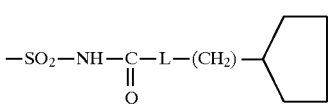
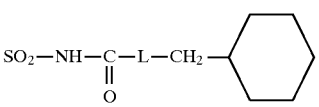
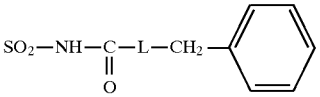
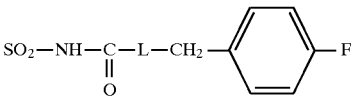
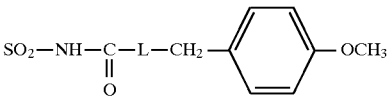
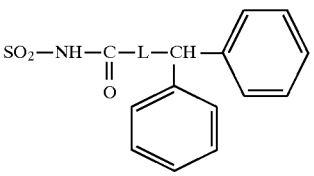
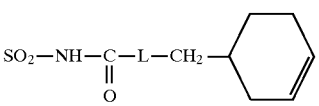

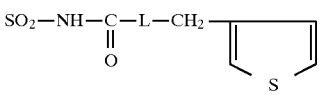
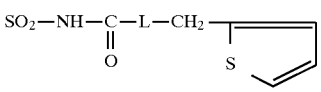

with L representing —O— or —NH—, it being understood that the sulphur atoms in the products of formula ($I_B$) can be optionally oxidized in the form of the sulphone or the sulphoxide, said products of formula ($I_B$) being in all the possible racemic, enantiomeric and diastereoisomeric isomer forms as well as the addition salts with mineral and organic acids or with mineral and organic bases of said products of formula ($I_B$).

A more particular subject of the invention is the products of formula (I), ($I_A$) or ($I_B$) as defined above, corresponding to formula ($I_D$) and corresponding to the products of formula (I) in which $R_1$ represents a linear or branched alkyl or alkylthio radical containing at most 4 carbon atoms, $R_2$ represents an alkylthio radical or a

radical in which Z represents a free, salified or esterified carboxy radical, $R_3$ represents the

radical in which $X_D$ represents an oxygen atom or a radical

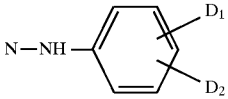

in which $D_1$ and $D_2$, identical or different, represent a halogen atom or a nitro radical, and $R_{5D}$ represents i) the —$CHY_1Y_2$ radical in which $Y_1$ represents a hydrogen or halogen atom and $Y_2$ represents a free, salified, amidified or esterified carboxy radical, linear or branched alkylthio, alkylsulphone and alkylsulphoxide radicals containing at most 6 carbon atoms, or phenylthio, phenylsulphone or phenylsulphoxide radicals, ii) the

radical in which $Y_3$ represents an optionally salified hydroxyl radical, linear or branched alkoxy or alkylthio radicals containing at most 6 carbon atoms, iii) when $X_D$ represents an oxygen atom, $R_{5D}$ represents an amino radical optionally substituted by a tetrazolyl radical or by one or two linear or branched alkyl radicals containing at most 6 carbon atoms, themselves optionally substituted by one or more phenyl or cyclohexyl radicals, c) when $X_D$ represents an oxygen atom, $R_{5D}$ represents a radical

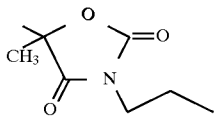

$R_4$ represents one of the following radicals: —SO$_2$—NH$_2$, —SO$_2$—N=CH—N(CH$_3$)$_2$,

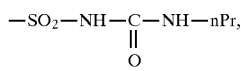

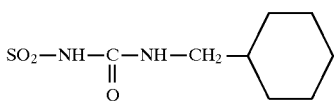

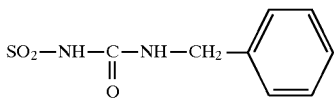

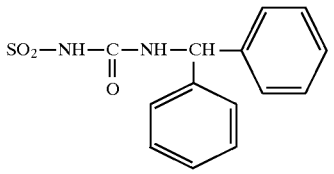

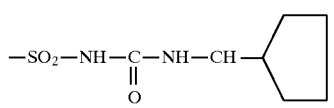

—SO$_2$—NH—CO$_2$Et, —SO$_2$—NH—CO$_2$H,

SO$_2$—NH—CO$_2$Pr,

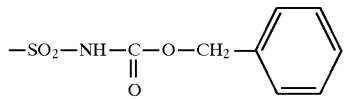

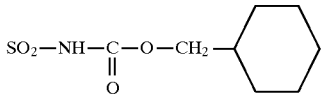

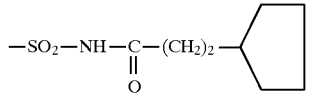

it being understood that the sulphur atoms in the products of formula ($I_D$) can be optionally oxidized in the form of the sulphone or sulphoxide, said products of formula ($I_D$) being in all the possible racemic, enantiomeric and diastereoisomeric isomer forms as well as the addition salts with mineral and organic acids or with mineral and organic bases of said products of formula ($I_D$).

Among the products which are a subject of the invention, there can be mentioned quite particularly the products of formula (I) corresponding to the following formulae:

2-butyl 1-((2'-(((((cyclohexylmethyl) amino) carbonyl) amino) sulphonyl) (1,1'-biphenyl) 4-yl) methyl) 4-methylthio alpha-oxo-1H-imidazole 5-acetic acid, ethyl 2-butyl 4-(methylthio) beta-oxo-1-((2'-(((( (propylamino) carbonyl) amino) sulphonyl) (1,1'-biphenyl) 4-yl) methyl) 1H-imidazole 5-propanoate, 2-butyl 4-(methylthio) 1-((2'-(((((propylamino) carbonyl) amino) sulphonyl) (1,1'-biphenyl) 4-yl) methyl) N-(1H-tetrazol-5-yl) 1H-imidazole 5-carboxamide, 2-butyl 4-(methylthio) alpha-oxo-1-((2'-(((((phenylmethyl) amino) carbonyl) amino) sulphonyl) (1,1'-biphenyl) 4-yl) methyl) 1H-imidazole 5-acetic acid, 4'-((2-butyl 5-(2-(methylsulphinyl) acetyl) 4-(methylthio) 1H-imidazol-1-yl) methyl) N-(((phenylmethyl) amino) carbonyl) (1,1'-biphenyl) 2-sulphonamide, 4-(methylthio) 1-((2'-(((((phenylmethyl) amino) carbonyl) amino) sulphonyl) (1,1'-biphenyl) 4-yl) methyl) 2-propyl-N-(2H-tetrazol 5-yl) 1H-imidazole 5-carboxamide, 2-butyl 4-(methylthio) alpha oxo N-(phenylmethyl) 1-((2'-( ((((phenylmethyl) amino) carbonyl) amino) sulphonyl) (1,1'-biphenyl) 4-yl) methyl) 1-H-imidazole 5-acetamide, 4'-((4-(methylthio) 5-(2-(phenylsulphinyl) acetyl) 2-propyl 1H-imidazol-1-yl) methyl N-(((phenylmethyl) amino) carbonyl) (1,1'-biphenyl) 2-sulphonamide, ethyl 2-butyl 4-(methylthio) beta-oxo 1-((2'-(((( (phenylmethyl) amino) carbonyl) amino) sulphonyl) (1,1'-biphenyl) 4-yl) methyl) 1H-imidazol-5-propanoate, 4'-((2-butyl 5-(2-((4-fluorophenyl) sulphonyl) acetyl) 4-(methylthio) 1H-imidazol 1-yl) methyl) N-(( (phenylmethyl) amino) carbonyl) (1,1'-biphenyl) 2-sulphonamide, 2-butyl 4'-((4-(methylthio) 5-((1H-tetrazol 5-yl) carbonyl) 1H-imidazol 1-yl) methyl) N-(((phenylmethyl) amino) carbonyl) (1,1'-biphenyl) 2-sulphonamide, 4'-((2-butyl 4-(methylthio) 5-((1H-tetrazol-5-yl) acetyl) 1H-imidazol-1-yl) methyl) N-(((phenylmethyl) amino) carbonyl) (1,1'-biphenyl) 2-sulphonamide, 4'-((4-(methylthio) 5-((phenylsulphinyl) acetyl) 2-propyl 1H-imidazol-1-yl) methyl) N-(((2-thienylmethyl) amino) carbonyl) (1,1'-biphenyl) 2-sulphonamide, (±) N-(((cyclopentylmethyl) amino) carbonyl) 4'-"4-(methylthio) 5-((phenylsulphinyl) acetyl) 2-propyl 1H-imidazol-1-yl) methyl) (1,1'-biphenyl) 2-sulphonamide, (±) N-(4'-((4-(methylthio) 5-((phenylsulphinyl) acetyl) 2-propyl 1H-imidazol 1-yl) methyl) (1,1'-biphenyl-2-yl) sulphonyl) cyclopentanepropanamide.

Also a subject of the invention is a preparation process for the products of formula (I), as defined above, characterized in that:

either a compound of formula (II):

in which $R'_1$ has the meaning indicated above for $R_1$, in which the optional reactive functions are optionally protected by protective groups and P represents a protective group of the nitrogen atom, is subjected to a halogenation reaction in order to obtain a compound of formula (III):

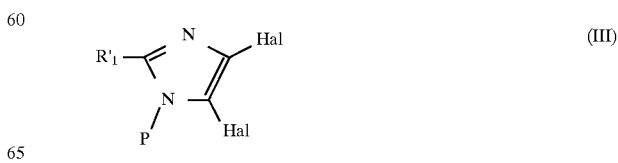

in which $R'_1$ and P have the meanings indicated above and Hal represents a halogen atom, which is subjected to a halogen-metal exchange reaction on one of the halogen atoms then to a reaction with a compound of formula (IV$_a$), (IV$_b$), (IV$_c$), (IV$_d$) or (IV$_e$):

(—S—R')$_2$  or (IV$_a$)

MeSO$_2$SR'  or (IV$_b$)

Cl—C—Oalk  or (IV$_c$)
 ‖
 O (alk-O)$_2$—C  or (IV$_d$)
 ‖
 O (alk-O—C)$_2$ (IV$_e$)
 ‖
 O in which R' has the meaning indicated above for R, in which the optional reactive functions are optionally protected by protective groups, and alk represents an alkyl radical containing at most 4 carbon atoms, in order to obtain the compound of formula (V):

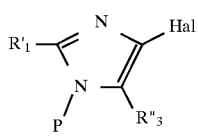
(V)

in which R'$_1$, P and Hal have the meanings indicated above and R"$_3$ represents S—R' or K—O-alk as defined above with K representing the

—C—
 ‖
 O or

—C—C—
 ‖  ‖
 O  O radical, which compound of formula (V) can be subjected to a halogen-metal exchange reaction on the halogen atom then to a reaction with a compound of formula (IV'$_a$), (IV'$_b$), (IV'$_c$), (IV'$_d$) or (IV'$_e$):

(—S—R")$_2$  or (IV'$_a$)

MeSO$_2$SR"  or (IV'$_b$)

Cl—C—Oalk'  or (IV'$_c$)
 ‖
 O (alk'-O)$_2$—C  or (IV'$_d$)
 ‖
 O (alk'-O—C)$_2$ (IV'$_e$)
 ‖
 O in which R", identical to or different from R', has the meaning indicated above for R, in which the optional reactive functions are optionally protected by protective groups and alk', identical to or different from alk, represents an alkyl radical containing at most 4 carbon atoms, in order to obtain the compound of formula (VII):

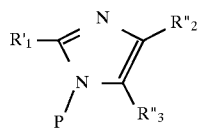
(VII)

in which R'$_1$ and P have the meanings indicated above, and R"$_2$ and R"$_3$, identical or different, represent —S—R', —S—R", —K-Oalk or —K-Oalk' as defined above in which R', R", alk, alk' and K have the meanings indicated above, from which product of formula (VII) the amine function blocked by P as defined above is released, then reacted with a compound of formula (VIII):

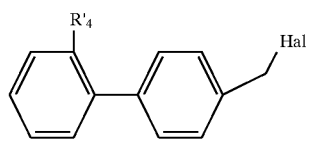
(VIII)

in which R'$_4$ has the meaning indicated above for R$_4$, in which the optional reactive functions are optionally protected by protective groups and Hal represents a halogen atom in order to obtain a product of formula (I$_1$):

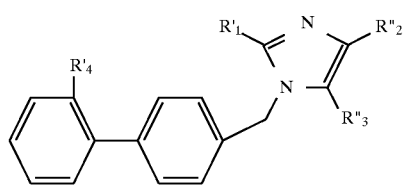
(I$_1$)

in which R'$_1$, R"$_2$, R"$_3$ and R'$_4$ have the meanings indicated above, or a compound of formula (IX):

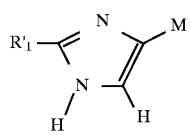
(IX)

in which R'$_1$ has the meaning indicated above and M represents a hydrogen atom or the R'$_2$ radical which has the meaning indicated above for R$_2$, in which the optional reactive functions are optionally protected by protective groups, is subjected to a reaction with the compound of formula (VIII) as defined above, in order to obtain a product of formula (X):

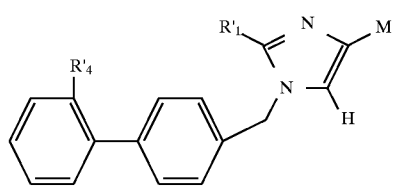
(X)

in which R'$_1$, M and R'$_4$ have the meanings indicated above, which products of formula (X) when M represents R'$_2$ as defined above, are subjected to a halogenation reaction in order to obtain the product of formula (XI):

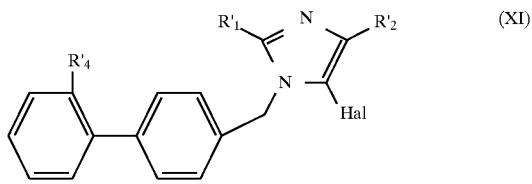

(XI)

in which R'$_1$, R'$_2$, R'$_4$ and Hal have the meanings indicated above, which is subjected to a halogen-metal exchange reaction then to a reaction with a compound of formula (XII):

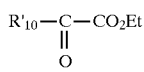

(XII)

in which R'$_{10}$ has the meaning indicated above for R$_{10}$, in which the optional reactive functions are optionally protected by protective groups, in order to obtain a product of formula (I$_2$):

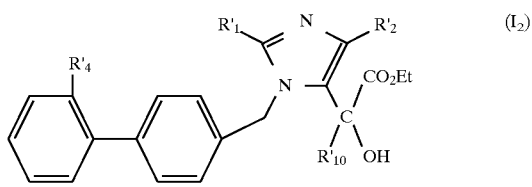

(I$_2$)

in which R'$_1$, R'$_2$, R'$_4$ and R'$_{10}$ have the meanings indicated above, and if desired either the product of formula (I$_2$) can be reacted with a compound of formula (XV):

(XV)

in which R'$_{11}$ has the meaning indicated above for R$_{11}$ in which the optional reactive functions are optionally protected by protective groups, in order to obtain the product of formula (I$_3$):

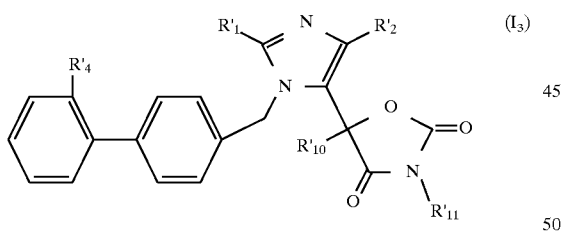

(I$_3$)

in which R'$_1$, R'$_2$, R'$_4$, R'$_{10}$ and R'$_{11}$ have the meanings indicated above, or the product of formula (I$_2$) is subjected to a saponification reaction in order to obtain the product of formula (I$_4$):

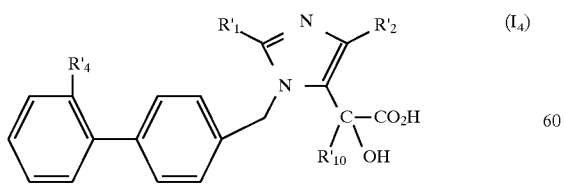

(I$_4$)

in which R'$_1$, R'$_2$, R'$_4$ and R'$_{10}$ have the meanings indicated above, which product of formula (I$_4$) can be reacted with COCl$_2$ in order to obtain the product of formula (I$_5$):

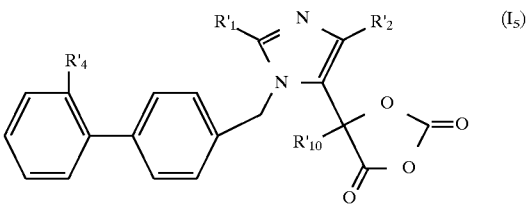

(I$_5$)

in which R'$_1$, R'$_2$, R'$_4$ and R'$_{10}$ have the meanings indicated above, or which product of formula (I$_4$) can be reacted with an aldehyde of formula R—CHO such as Cl$_3$C—CHO (CH$_3$)$_3$CCHO or also PhCHO, in order to obtain the product of formula (I$_6$):

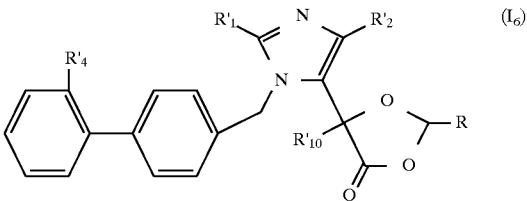

(I$_6$)

in which R'$_1$, R'$_2$, R'$_4$ and R$_{10}$ have the meanings indicated above or which product of formula (X) when M represents a hydrogen atom, can be subjected to a halogenation reaction in order to obtain the product of formula (XIV):

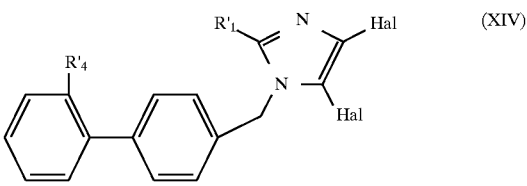

(XIV)

in which R'$_1$, R'$_4$ and Hal have the meanings indicated above, which can be subjected to a halogen-metal exchange reaction then to the action of a compound of formula (IV$_a$), (IV$_b$), (IV$_c$), (IV$_d$) or (IV$_e$) as defined above in order to obtain the product of formula (I$_7$):

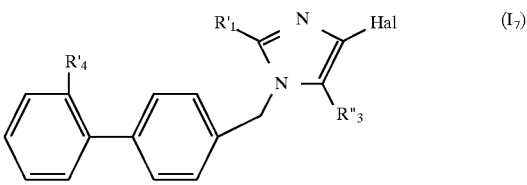

(I$_7$)

in which R'$_1$, R'$_4$, Hal and R''$_3$ have the meanings indicated above, which product of formula (I$_7$) can be subjected to a halogen-metal exchange reaction then to the action of a compound of formula (IV'$_a$), (IV'$_b$), (IV'$_c$), (IV'$_d$) or (IV'$_e$), as defined above, in order to obtain a product of formula (I$_8$):

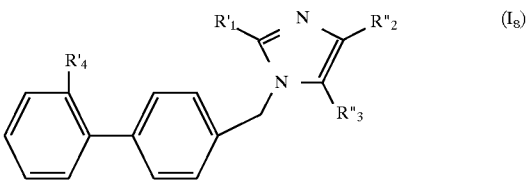

(I$_8$)

in which R'$_1$, R'$_4$, R''$_2$ and R''$_3$ have the meanings indicated above, or a compound of formula (XX):

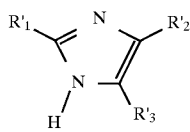

in which R'$_1$ and R'$_2$ have the meanings indicated above and R'$_3$ has the meaning indicated above for R$_3$ in which the optional reactive functions are optionally protected by protective groups, is subjected to a reaction with the compound of formula (VIII) as defined above, in order to obtain a product of formula (I'):

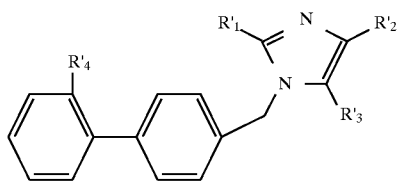

in which R'$_1$, R'$_2$, R'$_3$ and R'$_4$ have the meanings indicated above, which products of formulae (I$_1$), (I$_2$), (I$_3$), (I$_4$), (I$_5$), (I$_6$), (I$_7$), (I$_8$) and (I') can be products of formula (I) and which, in order to obtain the products or other products of formula (I), can be subjected, if desired and if necessary, to one or more of the following conversion reactions, in any order:

a) esterification of the acid function,
b) saponification of the ester function into an acid function,
c) conversion of the ester function into an acyl function,
d) conversion of the cyano function into an acid function,
e) conversion of the acid function into an amide function, then optionally into a thioamide function,
f) reduction of the carboxy function to an alcohol function,
g) conversion of the alkoxy function into a hydroxyl function, or also of the hydroxyl function into an alkoxy function,
h) oxidation of the alcohol function into an aldehyde, acid or ketone function,
i) conversion of the formyl radical into a carbamoyl radical,
j) conversion of the carbamoyl radical into a nitrile radical,
k) conversion of the nitrile radical into a tetrazolyl,
l) oxidation of the alkylthio or arylthio group into a corresponding sulphoxide or sulphone,
m) conversion of the sulphide, sulphoxide or sulphone function into a corresponding sulphoximine function,
n) conversion of the oxo function into a thioxo function,
o) conversion of the

radical into a

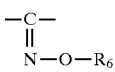

or

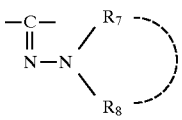

radical with R$_6$, R$_7$ and R$_8$ as defined above,
p) conversion of the acid function into a

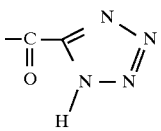

function,
q) conversion of the beta-keto-sulphoxide function into an alpha-keto thio ester function,
r) conversion of a carbamate into urea and in particular of a sulphonylcarbamate into sulphonylurea,
s) elimination of the protective groups which can be carried by the protected reactive functions,
t) salification by a mineral or organic acid or by a base in order to obtain the corresponding salt,
u) resolution of the racemic forms into resolved products, said products of formula (I) thus obtained being in all the possible racemic, enantiomeric and diastereoisomeric isomer forms.

Under the preferred conditions for implementing the invention, the halogenation reaction of the compounds of formulae (II) and (X) as defined above into the compounds of formula (III) and (XI) or (XIV) as defined above respectively, can be carried out under the usual conditions known to a man skilled in the art and in particular by bromination using N-bromosuccinimide in dichloromethane or also bromine in acetic acid.

Obtaining the corresponding compound of formula (V) can be achieved by the reaction of the compound of formula (III) as defined above with an organo-metallic compound such as n-butyllithium in a solvent such as tetrahydrofuran at a temperature of approximately −78° C. followed by the action of a compound of formula (IV$_a$), (IV$_B$), (IV$_C$), (IV$_d$) or (IV$_e$).

The reaction of the product of formula (V) as defined above with the compound of formula (IV'$_a$), (IV'$_b$) or (IV'$_c$) (IV'$_d$) or (IV'$_e$), as defined above, in order to obtain a compound of formula (VII) as defined above, can be achieved in an identical manner by using n-butyllithium as metallation agent.

The amine function of the compound of formula (VII) as defined above, protected by P as defined above, can be released under the usual conditions known to a man skilled in the art and in particular when P represents the —CH$_2$—O—(CH$_2$)$_2$—Si(CH$_3$)$_3$ radical, by the action of trifluoroacetic acid or also in the presence of a fluoride ion.

In the product of formula (VIII), Hal preferably represents a bromine atom but can also represent a chlorine or iodine atom.

The reaction of the product of formula (VIII) on the product of formula (VII) or (IX) or (XX), can be carried out in a solvent such as for example dimethylformamide or also dimethylacetamide, tetrahydrofuran, dimethoxyethane or dimethylsulphoxide under reflux of the solvent or at ambient temperature, preferably under agitation; the reaction is preferably carried out in the presence of a base such as for example sodium or potassium hydride or also sodium or potassium carbonate, sodium or potassium methylate or ethylate or tert-butylate.

Obtaining the compound of formula ($I_2$) as defined above is achieved by the action, on the magnesium-compound derivative of the compound of formula (XI), of the compound of formula (XII) as defined above in a solvent such as for example tetrahydrofuran or toluene.

The magnesium-compound derivative of the compound of formula (XI) is produced by the action of the compound of formula (XI) as defined above in which Hal can for example represent a bromine atom, with a magnesium compound such as for example isopropyl magnesium chloride, in a solvent such as for example toluene.

The reaction of the product of formula ($I_2$) as defined above with the compound of formula (XV) as defined above, to produce the product of formula ($I_3$) as defined above, can be carried out for example in acetone or tetrahydrofuran, in the presence of sodium or potassium bicarbonate or sodium or potassium carbonate.

The saponification reaction of the product of formula ($I_2$) as defined above, into the product of formula ($I_4$) as defined above, can be carried out according to the usual methods known to a man skilled in the art, such as for example in the presence of soda or potash or also caesium carbonate, in a solvent such as methanol or ethanol, dioxane or dimethoxyethane.

The product of formula ($I_4$) as defined above, can be cyclized into a product of formula ($I_5$) as defined above, in particular by reacting the product of formula ($I_4$), with phosgene in dichloromethane.

The conversion reaction of the product of formula ($I_4$) as defined above, into the product of formula ($I_6$) as defined above, can be carried out for example by reacting the product of formula ($I_4$), with an aldehyde in the presence of an acid such as tosylic acid, in toluene.

The conversion reaction of the product of formula (XIV) as defined above, into the product of formula ($I_7$) as defined above then into the product of formula ($I_8$), can be carried out under the same conditions as those defined for obtaining the products of formulae (V) and (VII) as defined above, from the product of formula (III) as defined above.

According to the values of $R'_1$, $R'_2$, $R''_2$, $R'_3$, $R''_3$ and $R'_4$, the products of formulae ($I_1$), ($I_2$), ($I_3$), ($I_4$), ($I_5$), ($I_6$), ($I_7$), ($I_8$) and (I') constitute or do not constitute products of formula (I) and can give products of formula (I), or be converted into other products of formula (I) by being subjected to one or more of reactions a) to u) indicated above.

Thus the various reactive functions which can be carried by certain compounds of the reactions defined above can, if necessary, be protected: they are for example the hydroxyl, acyl, free carboxy or also amino and monoalkylamino radicals which can be protected by the appropriate protective groups.

The following non-exhaustive list of examples of the protection of reactive functions can be mentioned:

the hydroxyl groups can be protected for example by alkyl radicals such as tert-butyl, trimethylsilyl, tertbutyldimethylsilyl, methoxymethyl, tetrahydropyrannyl, benzyl or acetyl, the amino groups can be protected for example by acetyl, trityl, benzyl, tert-butoxycarbonyl, phthalimido radicals or other radicals known in the chemistry of the peptides, the acyl groups such as the formyl group can be protected for example in the form of cyclic or non-cyclic ketals or thioketals such as dimethyl or diethylketal or ethylene dioxyketal, or diethylthioketal or ethylenedithioketal, the acid functions of the products described above can be, if desired, amidified by a primary or secondary amine for example in methylene chloride in the presence, for example, of 1-ethyl-3-(dimethylaminopropyl) carbodiimide hydrochloride at ambient temperature:

the acid functions can be protected for example in the form of esters formed with easily-cleavable esters such as benzyl or ter butyl esters or esters known in the chemistry of the peptides.

The reactions to which the products of formulae ($I_1$), ($I_2$), ($I_3$), ($I_4$), ($I_5$), ($I_6$), ($I_7$), ($I_8$) and (I'), as defined above, can be subjected, if desired or if necessary, can be carried out, for example, as indicated hereafter.

a) The products described above can, if desired, be subjected to, on the optional carboxy functions, to esterification reactions which can be carried out according to the usual methods known to a man skilled in the art.

b) The optional conversions of the ester functions into an acid function of the products described above can be, if desired, carried out under the usual conditions known to a man skilled in the art in particular by alkaline hydrolysis for example using soda or potash in an alcoholic medium such as, for example, in methanol or also by acid hydrolysis using hydrochloric or sulphuric acid.

c) The addition reaction on the

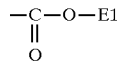

ester function in which $E_1$ can represent an optionally substituted and optionally protected alkyl or aryl radical into an acyl

function can be carried out in particular by the action of the carbonated anion

in which $E_2$, $E_3$ and $E_4$, identical or different, are chosen from the hydrogen atom, the following radicals: alkyl, alkylthioaryl, alkylsulphoxide, arylsulphoxide, alkylsulphone, arylsulphone, acyl, free, salified, esterified or amidified carboxy, the alkyl, alkylthio and aryl radicals being optionally substituted and optionally protected as is indicated above.

Such a reaction is carried out in particular as is described in the experimental part, or according to the usual methods known to a man skilled in the art.

d) The optional cyano functions of the products described above can be, if desired, converted into an acid function under the usual conditions known to a man skilled in the art for example by double hydrolysis carried out in an acid medium such as for example in a mixture of sulphuric acid, glacial acetic acid and water, these three compounds preferably being in equal proportions, or also in a mixture of soda, ethanol and water under reflux.

e) The conversion reaction of the acid function into an amide function can in particular be carried out by first forming an acid chloride according to the usual conditions known to a 10 man skilled in the art and for example by the action of SOCl$_2$ then amidification as indicated above, or also by direct amidification of the above acid.

In particular the radical

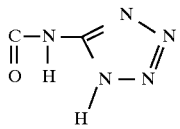

can be obtained by converting the acid function into an acid chloride, in particular by the action of SOCl$_2$ in a solvent such as for example toluene, or benzene, then by reacting the amine

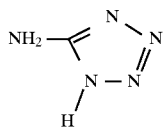

The amide thus obtained can then if desired be converted into a thioamide by the action in particular of LAWESSON reagent in toluene, f) The optional free or esterified carboxy functions of the products described above can be, if desired, reduced to an alcohol function by methods known to a man skilled in the art: the optional esterified carboxy functions can be, if desired, reduced to an alcohol function by methods known to a man skilled in the art and in particular by lithium aluminium hydride in a solvent such as for example tetrahydrofuran or also dioxane or ethyl ether.

The optional free carboxy functions of the products described above can be, if desired, reduced to an alcohol function in particular by boron hydride.

g) The optional alkoxy functions such as in particular methoxy of the products described above can be, if desired, converted into a hydroxyl function under the usual conditions known to a man skilled in the art for example by boron tribromide in a solvent such as for example methylene chloride, by pyridine hydrobromide or hydrochloride or also by hydrobromic or hydrochloric acid in water or trifluoroacetic acid under reflux.

h) The optional alcohol function of the products described above can be, if desired, converted into an aldehyde or acid function by oxidation under the usual conditions known to a man skilled in the art such as for example by the action of manganese oxide in order to obtain the aldehydes or of Jones reagent to access the acids.

i) j) The conversion reactions of the formyl radical into a carbamoyl radical and of the carbamoyl radical into a nitrile radical, are carried out in particular for R$_3$ and R$_4$ according to the usual conditions known to a man skilled in the art, such as for example, passage by the keto nitrile and displacement by an amine (Chem. Comm. 1971, p. 733).

k) The optional nitrile functions of the products described above can be, if desired, converted into tetrazolyl under the usual conditions known to a man skilled in the art such as for example by the cycloaddition of a metal azide such as for example sodium azide or a trialkyltin azide on the nitrile function as is indicated in the method described in the article referenced as follows: J. Organometallic Chemistry., 33, 337 (1971) KOZIMA S. et al.

l) The optional alkylthio or arylthio groups of the products described above can be, if desired, converted into corresponding sulphoxide or sulphone functions under the usual conditions known to a man skilled in the art such as for example by peracids such as for example peracetic acid or metachloroperbenzoic acid or also by ozone, oxone, sodium periodate in a solvent such as for example methylene chloride or dioxane at ambient temperature.

Obtaining the sulphoxide function can be encouraged by an equimolar mixture of the product containing an alkylthio or arylthio group and of the reagent such as in particular a peracid.

Obtaining the sulphone function can be encouraged by a mixture of the product containing an alkylthio or arylthio group with an excess of the reagent such as in particular a peracid.

m) The optional sulphide, sulphoxide or sulphone functions of the products described above can be, if desired, converted into the corresponding sulphoximine functions under the usual conditions known to a man skilled in the art: non-exhaustive examples of the preparation of products containing a sulphoximine function are described below.

Thus for example for the preparation of compounds such as N-(arylsulphonyl) sulphoximines and for example in the case where the aryl group is a toluene radical, the sulphoximine can be obtained by the action of paratoluenesulphonyl nitride on the corresponding sulphoxide i.e. —S(O)CH$_3$ preferably in the presence of copper as is indicated, for example, in the following reference:

J. A. C. S., 95, pp. 4287 (1973) JOHNSON C. R. et al.

Another method which is also used consists of treating N-tosylsulphilimine, itself prepared from the sulphide by the action, for example, of chloramine "T", by an oxidizing agent such as for example, sodium hypochlorite under phase transfer conditions as is indicated, for example, in the following reference:

J. Org. Chem., 49, pp. 2282 (1984) AKUTAGAWA K. et al.

n) The conversion reaction of the oxo function into a thioxo function can be achieved in particular by the LAWESSON reagent under the conditions defined above.

o) The conversion reaction of the

acyl radical into a

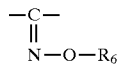

radical can in particular be carried out by condensation with a derivative of hydroxylamine, such as the —NH$_2$—O—R$_6$ compound in which R$_6$ has the meaning indicated above in an alcoholic solvent such as for example methanol or ethanol. The conversion reaction of the

acyl radical into a

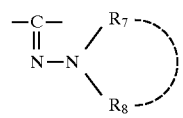

radical can in particular be carried out by condensation with a derivative of hydrazine, such as the compound

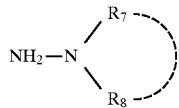

in which R$_7$ and R$_8$ have the meaning indicated above, in an alcoholic solvent (for example methanol or ethanol), p) The conversion reaction of the acid function into a tetrazolylcarboxy function can be carried out for example by preliminary conversion of the acid function into an acid chloride as indicated above, then by the action of cuprous cyanide, according to the usual conditions known to a man skilled in the art on the acid chloride thus obtained, in this way the

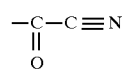

radical is obtained which can be converted into the radical

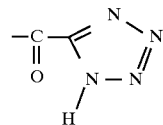

for example by the action of the compound Sn(Bu)$_3$N$_3$ in toluene, q) the conversion reaction of the beta keto sulphoxide function into an alpha keto thioester function, can be carried out by bromination in alpha position of the ketosulphoxide for example by the action of N-bromosuccinimide in for example methylene chloride then by a PUMMERER reaction carried out in a mixture of trifluoroacetic acid and methylene chloride or also a mixture of sulphuric acid and dioxane.

In particular, as defined above in c) and q), the following reaction diagram can be carried out:

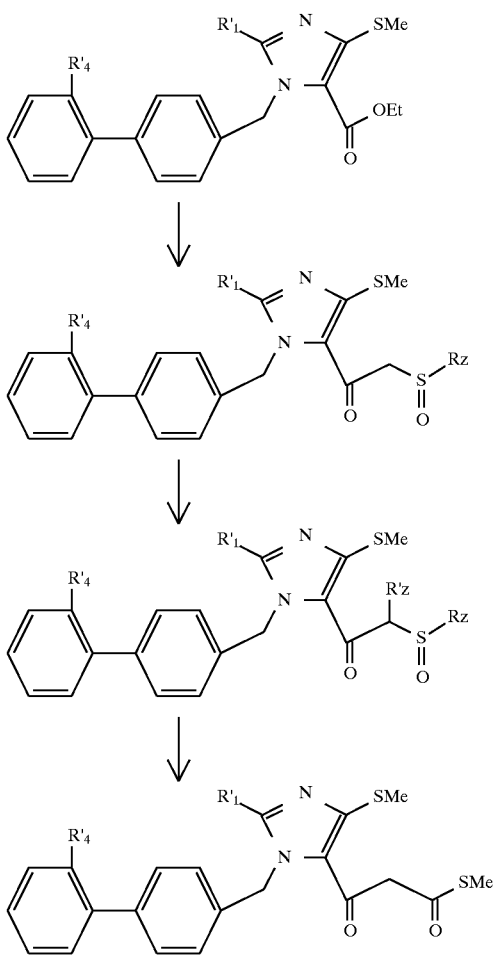

in which compounds R'$_1$ and R'$_4$ have the meanings indicated above, and Rz and R'z identical or different represent an optionally substituted alkyl or aryl radical as indicated above.

An illustration of this reaction diagram is given hereafter in the experimental part in Preparation 4.

r) The conversion reaction of a carbamate into urea and in particular of a sulphonylcarbamate into sulphonylurea, can be carried out for example under reflux of a solvent such as for example toluene in the presence of the suitable amine.

s) Elimination of the protective groups such as for example those indicated above can be carried out under the usual conditions known to a man skilled in the art in particular by acid hydrolysis carried out with an acid such as one of the following acids: hydrochloric, benzene sulphonic or paratoluene sulphonic, formic or trifluoroacetic or also by catalytic hydrogenation. The phthalimido group can be eliminated with hydrazine.

A list of different protective groups which can be used will be found for example in the Patent BF 2,499,995.

t) The products described above can, if desired, be subjected to salification reactions for example by a mineral or organic acid or by a mineral or organic base according to the usual methods known to a man skilled in the art.

u) The optional optically-active forms of the products described above can be prepared by resolution of the racemics according to the usual methods known to a man skilled in the art.

Illustrations of such reactions defined above are given in the preparation of the examples described hereafter.

The compounds of formula (I) as defined above as well as their addition salts with acids have useful pharmacological properties.

The products of formula (I) as defined above are endowed with antagonistic properties for the angiotensin II receptors and are thus in particular inhibitors of the effects of angiotensin II, especially of the vasoconstrictive effect and also of the trophic effect at the level of the myocytes.

These properties justify their use in therapeutics and a subject of the invention is also as medicaments, the products as defined by formula (I) above, said products of formula (I) being in all the possible racemic or optically-active isomer forms, as well as the addition salts with pharmaceutically acceptable mineral or organic acids of said products of formula (I).

A particular subject of the invention is as medicaments, the products of formulae ($I_A$), ($I_B$) and ($I_D$) as defined above, said products of formulae ($I_A$), ($I_B$) and ($I_D$) being in all the possible racemic or optically-active isomer forms, as well as the addition salts with pharmaceutically acceptable mineral or organic acids of said products of formulae ($I_A$), ($I_B$) and ($I_D$).

A more particular subject of the invention is, as medicaments, the products described hereafter in the examples and in particular the following products of formula (I):

2-butyl 1-((2'-(((((cyclohexylmethyl) amino) carbonyl) amino) sulphonyl) (1,1'-biphenyl) 4-yl) methyl) 4-methylthio alpha-oxo-1H-imidazole 5-acetic acid, ethyl 2-butyl 4-(methylthio) beta-oxo-1-((2'-(((( (propylamino) carbonyl) amino) sulphonyl) (1,1'-biphenyl) 4-yl) methyl) 1H-imidazole 5-propanoate, 2-butyl 4-(methylthio) 1-((2'-(((((propylamino) carbonyl) amino) sulphonyl) (1,1'-biphenyl) 4-yl) methyl) N-(1H-tetrazol-5-yl) 1H-imidazole 5-carboxamide, 2-butyl 4-(methylthio) alpha-oxo-1-((2'-(((((phenylmethyl) amino) carbonyl) amino) sulphonyl) (1,1'-biphenyl) 4-yl) methyl) 1H-imidazole 5-acetic acid, 4'-((2-butyl 5-(2-(methylsulphinyl) acetyl) 4-(methylthio) 1H-imidazol-1-yl) methyl) N-(((phenylmethyl) amino) carbonyl) (1,1'-biphenyl) 2-sulphonamide, 4-(methylthio) 1-((2'-(((((phenylmethyl) amino) carbonyl) amino) sulphonyl) (1,1'-biphenyl) 4-yl) methyl) 2-propyl-N-(2H-tetrazol 5-yl) 1H-imidazole 5-carboxamide, 2-butyl 4-(methylthio) alpha oxo N-(phenylmethyl) 1-((2'-( ((((phenylmethyl) amino) carbonyl) amino) sulphonyl) (1,1'-biphenyl) 4-yl) methyl) 1-H-imidazole 5-acetamide, 4'-((4-(methylthio) 5-(2-(phenylsulphinyl) acetyl) 2-propyl 1H-imidazol-1-yl) methyl N-(((phenylmethyl) amino) carbonyl) (1,1'-biphenyl) 2-sulphonamide, ethyl 2-butyl 4-(methylthio) beta-oxo 1-((2'-(((( (phenylmethyl) amino) carbonyl) amino) sulphonyl) (1,1'-biphenyl) 4-yl) methyl) 1H-imidazol-5-propanoate, 4'-((2-butyl 5-(2-((4-fluorophenyl) sulphonyl) acetyl) 4-(methylthio) 1H-imidazol 1-yl) methyl) N-(( (phenylmethyl) amino) carbonyl) (1,1'-biphenyl) 2-sulphonamide, 2-butyl 4'-((4-(methylthio) 5-((1H-tetrazol 5-yl) carbonyl) 1H-imidazol 1-yl) methyl) N-(((phenylmethyl) amino) carbonyl) (1,1'-biphenyl) 2-sulphonamide, 4'-((2-butyl 4-(methylthio) 5-((1H-tetrazol-5-yl) acetyl) 1H-imidazol-1-yl) methyl) N-(((phenylmethyl) amino) carbonyl) (1,1'-biphenyl) 2-sulphonamide, 4'-((4-(methylthio) 5-((phenylsulphinyl) acetyl) 2-propyl 1H-imidazol-1-yl) methyl) N-(((2-thienylmethyl) amino) carbonyl) (1,1'-biphenyl) 2-sulphonamide, (±) N-(((cyclopentylmethyl) amino) carbonyl) 4'-"4-(methylthio) 5-((phenylsulphinyl) acetyl) 2-propyl 1H-imidazol-1-yl) methyl) (1,1'-biphenyl) 2-sulphonamide, (±) N-(4'-((4-(methylthio) 5-((phenylsulphinyl) acetyl) 2-propyl 1H-imidazol 1-yl) methyl) (1,1'-biphenyl-2-yl) sulphonyl) cyclopentanepropanamide, as well as their addition salts with pharmaceutically acceptable mineral or organic acids The medicaments, which are a subject of the invention, can be used in the treatment of cardiovascular illnesses showing vasomotricity and total blood volume disorders: myocardial infarction and its consequences, cardiac insufficiency, renal insufficiency, angina pectoris, hyperaldosteronism, arterial hypertension and its consequences. These medicaments, which are a subject of the invention, could also be used for the treatment of glaucoma, atherosclerosis and different types of visceral spasms, and as neuronal protective substances or also in the prevention of post-angioplastic recurrence of stenosis.

In particular the medicaments, which are a subject of the invention, can be used for their anti-hypertrophic and anti-fibrotic effects at the cardiac and vascular levels. Quite particularly, they can be used for the treatment and prevention of cardiovascular disorders and in particular microcirculatory disorders associated with diabetes.

They can also be used in the treatment of certain gastro-intestinal and gynaecological disorders and in particular for a relaxing effect on the uterus.

The medicaments, which are a subject of the invention, can also be used in the treatment of memory disorders and disorders of the cognitive functions, as well as for anxiety.

The invention extends to the pharmaceutical compositions containing at least one of the medicaments as defined above, as active ingredient.

These pharmaceutical compositions can be administered by buccal, rectal route, by parenteral route or by local route as a topical application on the skin and mucous membranes or by injection by intravenous or intramuscular route.

These compositions can be solid or liquid and be presented in the pharmaceutical forms commonly used in human medicine, such as for example, plain or sugar-coated tablets, capsules, granules, suppositories, injectable preparations, ointments, creams, gels and aerosol preparations; they are prepared according to the usual methods. The active ingredient can be incorporated with excipients usually employed in these pharmaceutical compositions, such as talc, gum arabic, lactose, starch, magnesium stearate, cocoa butter, aqueous or non-aqueous vehicles, fatty substances of animal or vegetable origin, paraffin derivatives, glycols, various wetting, dispersing or emulsifying agents, preservatives.

The usual dose, which is variable according to the product used, the patient treated and the illness in question, can be, for example, from 1 to 100 mg per day for an adult, by oral route.

Certain starting products of formulae (II), (IX) and (XX) are known and can be prepared for example as indicated in the European Patent EP 168,950.

Other starting products of formulae (II), (IX) and (XX) can in particular be prepared as indicated in the European Patent EP 0465368 or in Preparations 1 to 6 described hereafter.

Some starting products of formulae (II), (IX) and (XX) are commercially-available such as for example:
the following products of formula (II):
2-phenylimidazole 2-methoxymethylimidazole
2-propylimidazole
2-isopropylimidazole
2-ethylimidazole
2-methylimidazole
the following products of formula (IX):
4-methyl 2-phenylimidazole
2,4-dimethylimidazole
2-ethyl 4-methylimidazole.

Examples of commercially-available products of formula (XX) are given in the Patent EP 0465368 or EP 0503162.

Also certain products of formulae (II), (IX) and (XX) can in particular be prepared from other products of formula (II) or (IX) for example by subjecting them to one or more of the reactions described in points a) to u) above carried out as indicated above.

Certain products of formulae (IX) and (XX) can also be obtained by the monohalogenation of the product of formula (II) as defined above into the product of formula ($P_1$):

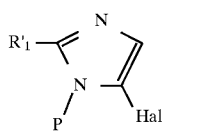

in which $R'_1$ and P have the meanings indicated above for the product of formula (II), which product of formula ($P_1$) can be reacted after exchange according to the halogen metal reaction known to a man skilled in the art with the suitable electrophile, according to methods known to a man skilled in the art and in particular as has been described above for passing from the product of formula (III) to the product of formula (V). By the same process, certain products of formulae (IX) and (XX) can also be obtained from the product of formula (III) as defined above. It can also be noted that the product of formula:

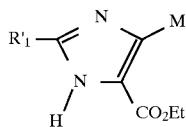

in which $R'_1$ and M have the meanings indicated above, described in EP 0465368, can be subjected to a thermal saponification reaction then to a decarboxylation in order to obtain a product of formula (IX) as defined above.

Such an illustration is given in the experimental part described hereafter.

The products of formula (III) in which $R'_1$ represents an alkylthio radical can be obtained either from the product of formula (II) as defined above as is described above, or from commercially-available products such as in particular 2,4, 5-tribromoimidazole, 4,5-dibromo 2-phenylimidazole, as has been described above for passing from the product of formula (III) to the product of formula (V).

The starting compounds of formula (VIII) may be commercially available or can be prepared according to the usual methods known to a man skilled in the art.

The starting products of formulae ($IV_a$), ($IV_b$), ($VI_a$), ($VI_b$), ($VI_c$), (XII) and (XV) are commercially available, in particular the products of formula ($IV_a$) such as sec-butyl disulphide, ethyl disulphide, isopropyl disulphide, methyl disulphide, benzyl disulphide, phenyl disulphide, propyl disulphide, the product of formula ($IV_b$) such as methyl methanethiosulphonate, the products of formula ($VI_a$) such as methyl chloroformate, benzyl chloroformate, isobutyl chloroformate, ethyl chloroformate, N-propyl chloroformate, the products of formula ($VI_b$) such as dimethyl carbonate, diethyl carbonate, the products of formula ($VI_c$) such as di-tert-butyl oxalate, diethyl oxalate, dimethyl oxalate, the products of formula (XII) such as ethyl thiophene 2-glyoxylate, ethyl 3-methyl 2-oxobutyrate, ethyl phenyl glyoxylate, methyl pyruvate, methyl benzoylformate, the products of formula (XV) such as methyl isocyanate, 2-carbomethoxyphenyl isocyanate, benzyl isocyanate, cyclohexyl isocyanate, N-propyl isocyanate, allyl iso-cyanate, phenyl isocyanate.

A preparation process for certain products of formula (VIII) is in particular described in the European Patent EP 0465368.

Examples of the preparation of the compounds of formula (VIII) are also described in the literature and examples are given in particular in the U.S. Pat. No. 4,880,804 or for example in the reference Chemistry and Industry 7 Sep. 1987 HOWARD and COLQUHOUN pp. 612–617.

Finally a subject of the present invention is as new industrial products and in particular as intermediate products necessary for the preparation of the products of formula (I), the compounds of formulae (II), (III), (V), (VII) when P represents —$CH_2$—O—$CH_2$—OMe, —$CH_2$—O—($CH_2$)$_2$—Si($CH_3$)$_3$, —$CH_2$—O—$CH_3$,

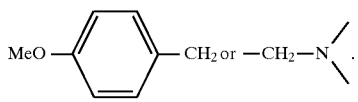

It has recently been shown that in fact two sub-types of angiotensin II receptors exist: $AT_1$ receptor and $AT_2$ receptor. Some products of formula (I) of the present invention have an affinity not only for receptor $AT_1$ but also for receptor $AT_2$.

Therefore a particular subject of the invention is the use of the products of formula (I) as defined above, for the preparation of pharmaceutical compositions intended for the treatment of illnesses resulting from an abnormal stimulation of AT1 and $AT_2$ receptors of angiotensin II.

A more particular subject of the invention is the use of the products of formula (I) as defined above, for the preparation of pharmaceutical compositions intended for the treatment of arterial hypertension, of post-infarction and of cardiac insufficiency and of post-angioplastic recurrence of stenosis.

A quite particular subject of the invention is the use of the products of formula (I) as defined above, for the preparation of pharmaceutical compositions intended for the treatment of renal insufficiency.

Also a subject of the invention is the use of the products of formula (I) as defined above, for the preparation of pharmaceutical compositions intended for the treatment and prevention of cardiovascular disorders and in particular microcirculatory disorders associated with diabetes.

The following examples illustrate the invention without however limiting it.

PREPARATION 1 ethyl 2-butyl alpha-hydroxy alpha-methyl 1-[(2'-(((dimethylamino) methylene) amino) sulphonyl) (1,1'-biphenyl) 4-yl) methyl]4-(methylthio) 1H-imidazole 5-acetate Stage A 4'-[(2-butyl 4-(methylthio) 1H-imidazol 1-yl) methyl]N-[(dimethylamino) methylene](1,1'-biphenyl) 2-sulphonamide a) 2-butyl 4-(methylthio) 1H-imidazole 760 mg of ethyl 2-n-butyl 4-methylthio imidazole 5-carboxylate, prepared as is described in the European Patent Application EP 0,465,368, is introduced into 15 cm³ of NaOH (2N). The reaction medium is taken to reflux and agitation is carried out for 24 hours. After cooling down, the medium is diluted with 50 cm³ of H₂O, extracted with 3×20 cm³ of CH₂Cl₂, washed with 20 cm³ of H₂O and dried. 535 mg of expected product is obtained.

M.p.=64° C.
IR Spectrum (CHCl₃)
Absence of C=O
=C—NH 3452 cm⁻¹
Conjugated system 1596–1502 cm⁻¹ b) 4'-[(2-butyl 4-(methylthio) 1H-imidazol 1-yl) methyl]N-[(dimethylamino) methylene](1,1'-biphenyl) 2-sulphonamide 5 g de 2-butyl 4-(methylthio) 1H-imidazole is dissolved in 120 cm³ of THF. Then 1.55 g of sodium hydride at 50% dispersion in oil is added slowly to the orange-coloured solution obtained. The temperature increases to 25° C. Agitation is carried out for 30 minutes at this temperature then 14 g of 4'-bromomethyl N-[(dimethylamino) methylene](1,1'-biphenyl) 2-sulphonamide is introduced. Agitation is carried out at ambient temperature until evolution ends, i.e. for approximately 3 hours, followed by taking up in water, extracting with ethyl acetate, separating by chromatography on silica eluting with ethyl acetate then impasting in iso ether, filtering and drying. In this way 9.35 g of expected product (colourless crystals) is obtained.

M.p.=148° C.
IR Spectrum: CHCl₃
Absence of =C—NH—

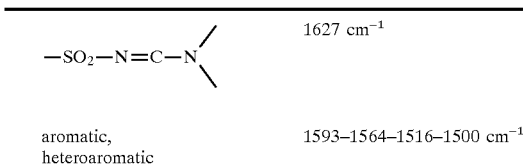

aromatic, heteroaromatic       1593–1564–1516–1500 cm⁻¹

Stage B

4'-[(5-bromo 2-butyl 4-(methylthio) 1H-imidazol 1-yl) methyl]N-[(dimethylamino) methylene](1,1'-biphenyl) 2-sulphonamide 10.4 g of the product obtained in Stage A above is dissolved in 450 cm³ of CH₂Cl₂ and 3.9 g of N-bromosuccinimide is added.

Agitation is carried out for approximately 15 minutes at ambient temperature, followed by washing with water and salt water, decanting, drying, filtering and driving off the solvent under vacuum at 50° C.

After impasting in iso ether, filtering and drying 11.8 g of expected product (colourless crystals) is obtained.

M.p.=158° C.
IR Spectrum: CHCl₃

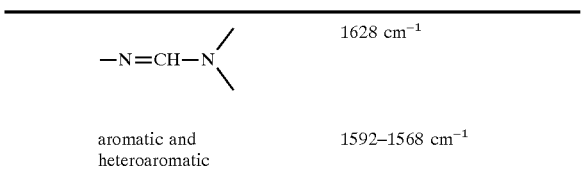

aromatic and heteroaromatic       1592–1568 cm⁻¹

Microanalysis:
Br
% calculated 14.54
% found 14.4–14.7

Stage C ethyl 2-butyl alpha-hydroxy alpha-methyl 1-[(2'-(((dimethylamino) methylene) amino) sulphonyl) (1,1'-biphenyl) 4-yl) methyl]4-(methylthio) 1H-imidazole 5-acetate 11.8 g of the product obtained in Stage B above is dissolved in 160 cm³ of THF. Then 17.5 cm³ of a 1M solution of isopropyl magnesium chloride in solution in ether is added without allowing the temperature to exceed 25° C. After agitation for approximately 30 minutes at ambient temperature, 4 cm³ of ethyl pyruvate is added slowly. Agitation is carried out for approximately 1 hour at ambient temperature, 1 cm³ of ethyl pyruvate is added and agitation is carried out again for approximately 1 hour.

The reaction medium is taken up in 200 cm³ of NH₄Cl in 10% solution and extraction is carried out with ethyl acetate, followed by drying, concentrating to approximately 200 cm³, filtering and drying the crystals obtained.

6 g of expected product (colourless crystals) is obtained.

M.p.=208°–210° C.
IR Spectrum: CHCl₃
Complex OH ~3530 cm⁻¹
C=O 1722 cm⁻¹
C=N 1626 cm⁻¹
Heterocycle+
aromatic 1565, 1518 cm⁻¹
UV spectrum:
1) In EtOH
  infl. 274 nm ε=3100
  infl. 231 nm ε=23000
2) In EtOH–HCl N/10
  infl. 228 nm ε=30000
  infl. 273 nm ε=3400

PREPARATION 2 ethyl 2-methyl 4-(methylthio) 1-[(2'-(((dimethylamino) methylene) amino) sulphonyl) (1,1'-biphenyl) 4-yl) methyl]alpha-oxo 1H-imidazole 5-acetate Stage A 4,5-dibromo 2-methyl 1-[(2-(trimethylsilyl) ethoxy) methyl]1H-imidazole The product is obtained by 2 consecutive reactions.
1) Protection stage of 2-methyl imidazole 6.8 g of 2-methyl imidazole is dissolved in 250 cm³ of THF and 4 g of sodium hydride at 50% in oil is added in small fractions. The reaction being exothermic, the temperature of the medium is maintained at ambient temperature for approximately 30 minutes.

Then 17.5 cm³ of SEM chloride is added dropwise to the reaction medium. After agitation for approximately 20 minutes at 20° C., the excess sodium hydride is hydrolyzed by the addition of THF with 20% H₂O.

The solution obtained is brought to dryness, taken up in ethyl acetate and washed with water. The organic phase thus collected is dried. A yellow oil is obtained which is purified by chromatography on silica with CH₂Cl₂-methanol (90-10) as eluant.

In this way 14 g of protected product is obtained.

2) Bromination

The protected product obtained above is dissolved in 250 cm³ of CH₂Cl₂. Then 25 g of N-bromo succinimide is added to this solution in small fractions.

Agitation is maintained for approximately 30 minutes at ambient temperature. The organic phase is washed with a solution of sodium bicarbonate, then abundantly with water. After drying and evaporating, 13.4 g of expected product (homogeneous yellow oil) is obtained.

IR Spectrum: CHCl₃
Absence of =C—NH—

| Conjugated system | 1520 cm$^{-1}$ |
|---|---|
| —Si— | 1253 cm$^{-1}$ |
| \| | 862 cm$^{-1}$ |
|  | 840 cm$^{-1}$ |

Stage B ethyl 2-methyl 1-[(2-(trimethylsilyl) ethoxy) methyl]5-(methylthio) alpha-oxo 1H-imidazole 4-acetate 3 g of the product obtained in Stage A above is dissolved in 20 cm³ of anhydrous THF, under an anhydrous atmosphere. This solution is then cooled down to −78° C. and 5.6 cm³ of 1.5 molar n-butyl lithium in hexane is added to it while maintaining the temperature at −78° C. Agitation is maintained at −78° C. for approximately 10 minutes.

Then 0.76 cm³ of dimethyl disulphide is introduced, then the temperature is allowed to slowly rise to 20° C. and agitation is carried out for approximately 30 minutes.

The reaction medium is again cooled down to −78° C., and as previously 5.6 cm³ of 1.5M n-butyl lithium in hexane is added to it. After agitation for approximately 10 minutes at −78° C., 5.5 cm³ of diethyl oxalate is introduced in one go. Agitation is maintained at ambient temperature for approximately 30 minutes. The reaction medium is then poured into ice-cooled water. Extraction is carried out with ethyl acetate, the organic phase is washed with a solution of sodium bicarbonate then with water and dried. A brown oil is recovered which is purified by chromatography on silica eluting with ethyl acetate-cyclohexane (50-50). 1.63 g of expected product (oil) is obtained.

IR Spectrum: CHCl₃

| C=O | 1738–1673 cm$^{-1}$ |
|---|---|
| Conjugated system | 1538 cm$^{-1}$ |
| \|<br>—Si—<br>\| | 1502 cm$^{-1}$ |

Stage C ethyl 2-methyl 5-(methylthio) alpha-oxo 1H-imidazole 4-acetate 1.6 g of the product obtained in Stage B above is dissolved in 30 cm³ of CH₂Cl₂, and 10 cm³ of trifluoroacetic acid is added. The reaction medium is then taken to reflux for approximately 10 hours. The solution is then brought to dryness, and the residue is taken up in water. The aqueous phase is alkalinized by the addition of sodium bicarbonate, followed by extraction with ethyl acetate, washing water then drying and 920 mg of expected product (yellow oil) is recovered which is used as it is in the continuation of the synthesis.

IR Spectrum: CHCl₃
=C—NH 3415 cm$^{-1}$
C=O 1716–1633 cm$^{-1}$
Conjugated system 1530–1502 cm$^{-1}$ Stage D ethyl 2-methyl 4-(methylthio) 1-[(2'-((( (dimethylamino) methylene) amino) sulphonyl) (1, 1'-biphenyl) 4-yl) methyl]alpha-oxo 1H-imidazole 5-acetate 880 mg of the product obtained in Stage C above is dissolved in 10 cm³ of anhydrous/DMF and 800 mg of potassium carbonate, then 2.2 g of 4'-bromomethyl N-[(dimethylamino) methylene](1,1'-biphenyl) 2-sulphonamide are added successively. Agitation is maintained for approximately 3 hours at ambient temperature. The yellow suspension thus obtained is poured into water, followed by extraction with ethyl acetate, washing with water then drying and a yellow resin is recovered which is purified on silica eluting with ethyl acetate.

In this way 1.17 g of expected product is obtained.

IR Spectrum: CHCl₃
Absence of =C—NH
C=O ester 1735 cm$^{-1}$
Other C=O 1629 cm$^{-1}$ (F)
C=N
Aromatic 1570 cm$^{-1}$
heteroatom 1516 cm$^{-1}$

PREPARATION 3 ethyl 1-[(2'-(aminosulphonyl) (1,1'-biphenyl) 4-yl) methyl]4-(methylthio) alpha-oxo 2-propyl 1H-imidazole 5-acetate Stage A 4,5-dibromo 2-propyl 1-[(2-(trimethylsilyl) ethoxy) methyl]1H-imidazole The operation is carried out as in Stage A of Preparation 2, by replacing 2-methyl 1H-imidazole with 2-propyl 1H-imidazole.

The product is obtained by 2 consecutive reactions.

1) Protection stage of 2-propyl imidazole 30 g of 2-propyl imidazole is dissolved in 500 cm³ of THF and 12.5 g of sodium hydride at 50% in oil is added in small fractions.

Then 53 cm³ of SEM chloride is added to the reaction medium, followed by hydrolysis using THF with 20% H₂O.

In this way 57.3 g of protected product is obtained.

2) Bromination

The protected product obtained above is dissolved in 500 cm³ of CH₂Cl₂. 93.5 g of N-bromo succinimide is added and 93.7 g of expected product is obtained.

IR Spectrum: CHCl₃
Absence of =C—NH—

| Conjugated system | 1520 cm$^{-1}$ |
|---|---|
| —Si— | 1253 cm$^{-1}$ |
| \| | 862 cm$^{-1}$ |
|  | 840 cm$^{-1}$ |

Stage B ethyl 2-n-propyl 1-[(2-(trimethylsilyl) ethoxy) methyl]5-(methylthio) alpha-oxo 1H-imidazole 4-acetate

36.7 g of the product obtained in Stage A above is introduced under an anhydrous atmosphere into 200 cm³ of THF, 63.7 cm³ of 1.5 Molar n-butyl lithium in hexane then 8.62 cm³ of dimethyl disulphide are added at −78° C., the reaction medium is left to rise to ambient temperature. Then as previously 63.7 cm³ of 1.5 Molar n-butyl lithium in hexane is added at −78° C. followed by 55 cm³ of ethyl oxalate. 11.75 g of expected product is obtained.

IR Spectrum: CHCl₃

| | |
|---|---|
| C=O | 1737–1672 cm⁻¹ |
| Conjugated system | 1527 cm⁻¹ |
| \|<br>—Si—<br>\| | 1501 cm⁻¹ |

Stage C ethyl 2-n-propyl 5-(methylthio) alpha-oxo 1H-imidazole 4-acetate

The operation is carried out as in Stage C of Preparation 2 starting with 11 g of the product obtained in Stage B above in 200 cm³ of CH₂Cl₂, and 40 cm³ of trifluoroacetic acid. 7.15 g of expected product is obtained.

IR Spectrum: CHCl₃
=C—NH 3413 cm⁻¹
C=O 1714–1633 cm⁻¹
Conjugated system 1524–1492 cm⁻¹

Stage D ethyl 2-n-propyl 4-(methylthio) 1-[(2'-((( (dimethylamino) methylene) amino) sulphonyl) (1, 1'-biphenyl) 4-yl) methyl]alpha-oxo 1H-imidazole 5-acetate

The operation is carried out as in Stage D of Preparation 2 starting with 7 g of the product obtained in Stage C above in 100 cm³ of DMF and 7.5 g of potassium carbonate and 15.6 g of 4'-(bromomethyl) N-[(dimethylamino) methylene] (1,1'-biphenyl) 2-sulphonamide. In this way 7.83 g of expected product is obtained.

IR Spectrum: CHCl₃
Absence of =C—NH
C=O ester 1735 cm⁻¹
Other C=O 1630 cm⁻¹ (F)
C=N

Stage E ethyl 1-[(2'-(aminosulphonyl) (1,1'-biphenyl) 4-yl) methyl]2-propyl 4-(methylthio) alpha-oxo 1H-imidazole 5-acetate

The operation is carried out as in Stage A of Example 2 starting with 7.8 g of the product obtained in Stage D above, in 100 cm³ of ethanol and 30 cm³ of concentrated HCl and in this way 3.6 g of expected product is obtained.

IR Spectrum CHCl₃
—NH₂ 3443–3343 cm⁻¹
C=O 1734–1627 cm⁻¹
Aromatic 1593 cm⁻¹
Heteroatom 1565 cm⁻¹
NH₂ def. 1542 cm⁻¹

PREPARATION 4

S-methyl 1-[(2'-(aminosulphonyl) (1,1'-biphenyl) 4-yl) methyl]2-butyl 4-(methylthio) alpha-oxo 1H-imidazole 5-ethane thioate

Stage A

4'-[(2-butyl 5-((methylsulphinyl) acetyl) 4-(methylthio) 1H-imidazol 1-yl) methyl](1,1'-biphenyl) 2-sulphonamide

Initially the anion of DMSO is prepared by introducing 3.36 g of sodium hydride at 50% in oil. The NaH has its oil removed by 3 successive washings with pentane, followed by drying, 70 cm³ of anhydrous dimethylsulphoxide is added and the mixture is heated at 75° C., for approximately 1 hour. The temperature is then reduced to 0° C. and then the anion of DMSO thus formed, 70 cm³ of anhydrous THF and 9.5 g of ethyl 2-butyl 1-[(2'-((((dimethylamino) methylene) amino) sulphonyl) (1,1'-biphenyl) 4-yl) methyl]4-(methylthio) 1H-imidazole 5-carboxylate, prepared as is indicated in the European Patent Application EP 0,503,162, dissolved in 70 cm³ of anhydrous THF, are added. Then the reaction medium is left to rise to ambient temperature and agitation is carried out for approximately ½ hour. The reaction mixture is then poured into 400 cm³ of H₂O.

The solution is acidified to pH 2 with 2N HCl, followed by extraction with 4×200 cm³ of methylene chloride and the organic phase is washed with 4×100 cm³ of distilled H₂O. The organic phase is dried, filtered and evaporated.

Purification is carried out on silica eluting with CH₂Cl₂-methanol (9-1) and 7.5 g of expected product is recovered.

IR Spectrum in CHCl₃

| | |
|---|---|
| Absence of SO₂N = —N⟨ | |
| NH₂ | 3440–3340 cm⁻¹ |
| C=O | 1628 cm⁻¹ |
| Aromatic + Heterocycle | 1545–1525–1495 cm⁻¹ |
| SO₂ | 1345–1165 cm⁻¹ |
| SO | 1050 cm⁻¹ |

Stage B

4'-[[5-[bromo (methylsulphinyl) acetyl]2-butyl 4-(methylthio) 1H-imidazol 1-yl]methyl] (1,1'-biphenyl) 2-sulphonamide

1 g of the product obtained in Stage A above and 530 mg of K₂CO₃ are introduced. Then 10 cm³ of anhydrous CH₂Cl₂ is added, the temperature of the medium is taken to 0° C. and 342 mg of N-bromo succinimide dissolved in the minimum amount of anhydrous CH₂Cl₂ is added dropwise. Then 100 cm³ of CH₂Cl₂ is added and the organic phase is washed with 3×200 cm³ of distilled water, and 1×100 cm³ of saturated NaCl, followed by drying, filtering and concentrating to dryness.

1.09 g of expected product is obtained.

IR Spectrum in CHCl₃
NH₂ 3440–3344 cm⁻¹
>=O 1634 cm⁻¹
Conj. system 1542–1520 cm⁻¹

+Aromatic
+NH$_2$
Stage C

S-methyl 1-[(2'-(aminosulphonyl) (1,1'-biphenyl) 4-yl) methyl]2-butyl 4-(methylthio) alpha-oxo 2-propyl 1H-imidazole 5-ethane thioate 6.8 g of the product obtained in Stage B above is dissolved in 60 cm$^3$ of a mixture of 25 cm$^3$ TFA—75 cm$^3$ CH$_2$Cl$_2$ and taken to reflux of the methylene chloride, for approximately 5 hours. The reaction is neutralized by treating with a saturated solution of NaHCO$_3$ to pH 5–6, followed by extraction with 2×200 cm$^3$ of ethyl acetate, washing with 1×100 cm$^3$ of saturated NaCl, drying, filtering and concentrating to dryness. Purification is carried out on silica, eluting with AcOEt-cyclohexane (5-5). In this way 2.7 g of expected product is recovered.

IR Spectrum in CHCl$_3$
NH$_2$ 3445–3350 cm$^{-1}$
>=O 1670–1614 cm$^{-1}$
Aromatic 1542 cm$^{-1}$–1518 cm$^{-1}$
+heteroaromatic
+NH$_2$ dif.

PREPARATION 5 ethyl 1-[(2'-(aminosulphonyl) (1,1'-biphenyl) 4-yl) methyl]4-(methylthio) 2-propyl 1H-imidazole 5-carboxylate Stage A ethyl cyano-[(1-oxobutyl) amino]acetate 5 g of ethyl (hydroxyimino) cyanoacetate, 40 cm$^3$ of tetrahydrofuran, 11.5 cm$^3$ of butyric anhydride and 2.5 g of platinum ae mixed together and agitation is carried out under a hydrogen atmosphere until saturation. After filtering and rinsing with 5×15 cm$^3$ of ethyl ether, the ether is evaporated off, 200 cm$^3$ of essence G is added little by little, followed by separating, washing with 3×10 cm$^3$ of essence G and drying at approximately 75° C. The resultant product is concentrated to ~10 cm$^3$, 50 cm$^3$ of essence G is added, and the whole is left to crystallize for 30 minutes at ambient temperature, followed by separating, washing with 3×3 cm$^3$ of essence G and drying at approximately 75° C. 5,73 g of product is obtained.

M.p.=110° C.
Recrystallization for analyses 540 mg of the product obtained is dissolved in 50 cm$^3$ of isopropyl ether under reflux, followed by filtering, concentrating, leaving for approximately 1 hour at rest at ambient temperature, separating, washing with isopropyl ether and drying. 440 mg of expected product is obtained.
M.p.=110° C.

| Microanalysis for C$_9$H$_{14}$N$_2$O$_3$ = 198.22 | | | | |
|---|---|---|---|---|
| | C | H | N | O |
| % calculated | 54.53 | 7.12 | 14.13 | 24.22 |
| % found | 54.5 | 7.2 | 14.0 | |

IR Spectrum CHCl$_3$
=C—NH ~3430 cm$^{-1}$
—C≡N ~2245 cm$^{-1}$
C=O 1758 cm$^{-1}$ ester
1692 cm$^{-1}$ amide
Amide II 1492 cm$^{-1}$
Stage B ethyl 3-amino 2-[(1-oxobutyl) amino]3-(methylthio) 2-propenoate 1.4 ml of triethylamine is added to a solution of 20 g of the nitrile obtained in Stage A above, in 400 ml of ethanol, the reaction medium is cooled down to approximately −10° C. and approximately 22 g of methylmercaptan is introduced by bubbling through. Agitation is carried out for approximately 72 hours at 0° C. The excess methanethiol is eliminated, the ethanol is driven off, followed by impasting in essence G, filtering and drying. 24.3 g of expected product (colourless crystals) is obtained.

M.p.$_{K115}$=120°–124° C.

| Microanalysis for C$_{10}$H$_{18}$N$_2$O$_3$S = 246.33 | | | | | |
|---|---|---|---|---|---|
| | C | H | N | S | O |
| % calculated | 48.76 | 7.37 | 11.37 | 13.02 | 19.49 |
| % found | 48.6 | 7.5 | 11.4 | 12.6 | — |

IR Spectrum CHCl$_3$
=C—NH$_2$ 3500, 3412 cm$^{-1}$
=C—NH 3365, 3275 cm$^{-1}$
C=O complex 1665 cm$^{-1}$
C=C and NH$_2$ def. 1592 cm$^{-1}$
Amide II 1488 cm$^{-1}$
UV spectrum in EtOH
Max. 220 nm ε=5500
Max. 291-292 ε=19400

Stage C ethyl 4-(methylthio) 2-propyl 1H-imidazole 5-carboxylate

A solution of 12.9 g of 4-dimethylaminopyridine in 90 cm$^3$ of methylene chloride is added to 20.1 g of phosphorus pentachloride in 300 cm$^3$ of methylene chloride, cooled down to approximately −70° C.

The reaction medium is maintained for approximately another 15 minutes at approximately −70° C. then a solution of 12 g of the product obtained in Stage B above in 120 cm$^3$ of methylene chloride is added. The reaction medium is left to return to ambient temperature and maintained under agitation for approximately 22 hours.

The reaction mixture is poured into 2.5 litres of water+ice and is neutralized by the addition of approximately 60 g of sodium bicarbonate. Agitation is carried out again for approximately 30 minutes, followed by decanting, extraction with 500 cm$^3$ of CH$_2$Cl$_2$, washing with salt water, drying and the solvent is driven off at approximately 50° C. Purification is carried out by chromatography on silica eluting with CH$_2$Cl$_2$-AcOEt (90-10) then CH$_2$Cl$_2$-AcOEt (80-20). The solvents are driven off at approximately 50° C., followed by impasting in essence G, filtering and drying. 7.4 g of expected product (colourless crystals) is obtained.

M.p.$_{K95}$=85° C.

| Microanalysis Concordance for $C_{10}H_{16}N_2O_2S$ = 228.32 | | | | |
|---|---|---|---|---|
| | C | H | N | S | O |
| % calculated | 52.61 | 7.06 | 12.27 | 14.04 | 14.02 |
| % found | 52.7 | 7.3 | 12.2 | 14.0 | |

IR Spectrum CHCl$_3$
=C—NH 3440–3260 cm$^{-1}$
complex C=) max. ~1672 cm$^{-1}$
Heterocycle 1542–1498 cm$^{-1}$
UV spectrum in EtOH
Max. 213–214 nm $\epsilon$=14500
Infl. 229 nm $\epsilon$=7200
Max. 286 nm $\epsilon$=12200
UV spectrum in EtOH/HCl N/10
Max. 238 nm $\epsilon$=6800
Max. 277 nm $\epsilon$=9600
by basic return →max. 296 nm.

Stage D ethyl 1-[(2'-((((dimethylamino) methylene) amino) sulphonyl) (1,1'-biphenyl) 4-yl) methyl]4-(methylthio) 2-propyl 1H-imidazole 5-carboxylate 8.1 g of the product obtained in Stage C above is dissolved in 80 cm$^3$ of dimethylformamide and 16.1 g of 4'-(bromomethyl) N-[(dimethylamino) methylene](1,1'-biphenyl) 2-sulphonamide and 4.9 g of potassium carbonate are added. Agitation is carried out at ambient temperature for approximately 24 hours. The DMF is driven off at 50° C., followed by impasting in water, filtering, washing with water and drying at approximately 60° C.

After impasting in 240 cm$^3$ of AcOEt, under agitation for approximately 30 minutes at approximately 50° C., 160 cm$^3$ of hexane is added followed by filtering and drying. 14 g of expected product (colourless crystals) is obtained.

M.p.$_{K163}$: 182° C.
IR Spectrum CHCl$_3$
Absence of =C—NH
C=O 1690 cm$^{-1}$
C=N 1628 cm$^{-1}$
Heterocycle 1504–1565 cm$^{-1}$
UV spectrum in EtOH
Infl. 230 nm $\epsilon$=32000
Max. 287 nm $\epsilon$=15500

Stage E ethyl 1-[(2'-(aminosulphonyl) (1,1'-biphenyl) 4-yl) methyl]4-(methylthio) 2-propyl 1H-imidazole 5-carboxylate 11.2 g of the product obtained in Stage D above is mixed with 200 cm$^3$ of ethanol and 100 cm$^3$ of concentrated hydrochloric acid. The reaction medium is heated under reflux for approximately 2 hours. The ethanol is evaporated off, followed by dilution by the addition of 400 cm$^3$ of water, alkalinization under agitation by the addition of caustic soda lye and extraction with ethyl acetate. After washing water and salt water, drying and filtering, the solvent is driven off at approximately 50° C.

Purification is carried out by chromatography on silica eluting with AcOEt 60 Hexane 40. 9.3 g of expected product (colourless crystals) is obtained. M.p.$_{K135}$=130°–132° C.
IR Spectrum CHCl$_3$
Absence of starting product
C=O 1689 cm$^{-1}$
NH$_2$ 3444–3340 cm$^{-1}$
Conjugated system
+aromatic 1618–1590–1560–1540–1508 cm$^{-1}$
NH$_2$ def.
UV spectrum in EtOH
Infl. 210 nm $\epsilon$=45000
Infl. 234 nm $\epsilon$=17000
Max. 286 nm $\epsilon$=15000

PREPARATION 6

Stage A

2,4,5-tribromo 1-[(2-(trimethylsilyl) ethoxy) methyl]1H-imidazole 3.04 g of tribromoimidazole is dissolved in 20 cm$^3$ of anhydrous THF. 550 mg of NaH at 50% in oil is added in small portions. After 20 minutes at ambient temperature, 1.95 ml of 2-(trimethylsilyl) ethoxy methyl chloride is added. After 30 minutes at ambient temperature, the reaction medium is hydrolyzed with a saturated solution of NH$_4$Cl, followed by extraction with AcOEt, drying and evaporating to dryness. Chromatography is carried out on silica eluting with cyclohexane/AcOEt (9-1) and 4.2 g of expected product (oil) is recovered.

Stage B

2n-propylthio 4,5-dibromo 1-[(2-(trimethylsilyl) ethoxy) methyl]1H-imidazole 3.48 g of the product obtained in Stage A is dissolved in 25 cm$^3$ of ether. 3 ml of a 3M solution of EtMgBr in ether is added. After 15 minutes at ambient temperature, 2.5 cm$^3$ of n-dipropyl disulphide then 40 cm$^3$ of anhydrous THF are added. The ether is distilled off and the reaction medium is left for 20 hours under reflux of THF. Hydrolysis is carried out with saturated NH$_4$Cl followed by extraction with AcOEt, drying and evaporating to dryness.

After chromatography eluting with (cyclohexane-AcOEt (9-1)), 2.7 g of expected product (oil) is obtained.

Stage C

2n-propylthio 4-bromo 5-methylthio 1-[(2-(trimethylsilyl) ethoxy) methyl]1H-imidazole 2.4 g of the expected product from Stage B is dissolved in 25 cm$^3$ of anhydrous THF. 3 ml of a 3M solution of EtMgBr in ether is added. After 1 hour at ambient temperature, 1.08 cm$^3$ of dimethyl disulphide is added and the reaction medium is left for 1 hour at ambient temperature followed by hydrolysis with saturated NH$_4$Cl, extraction with AcOEt, drying and evaporating to dryness.

After chromatography eluting with cyclohexane-AcOEt (9-1), 1.83 g of expected product (oil) is obtained.

Stage D

2n-propylthio 5-methylthio 1-[(2-(trimethylsilyl) ethoxy) methyl]1H-imidazole 7.94 g of the product obtained in Stage C above is introduced at ambient temperature into 80 cm$^3$ of anhydrous THF, followed by cooling down to −78° C. and 13.75 cm$^3$ of a 1.6M n-butyllithium solution in hexane is added. After 10 minutes, 15 cm³ of ethyl chloroformate is added, followed by agitation for another 15 minutes at −78° C. 60 cm³ of water is added, the reaction medium is left to return to ambient temperature, the THF is evaporated off, 10 cm³ of 32% soda is added to destroy the excess ethyl chloroformate, followed by extraction with 3×200 cm³ of AcOEt, washing with 2×80 cm³ of water, drying, filtering and evaporating.

After chromatography on silica eluting with AcOEt-cyclo (2-8), 4.34 g of expected product is recovered.

IR Spectrum: in CHCl₃

═O 0 1708 cm⁻¹
C═C 1504 cm⁻¹
C═N

Stage E ethyl 2n-propylthio 5-methylthio imidazole 4-carboxylate 4.34 g of the product obtained in Stage D above, 40 cm³ of EtOH, 28 cm³ of water, 28 cm³ of fuming HCl are mixed together at ambient temperature. The reaction medium is heated for two hours at 70° C. using a bath. The EtOH is evaporated off, the medium is alkalinized with approximately 20 cm³ of 32% soda, the pH is returned to ~6, with 1 to 2 cm³ of acetic acid, followed by extraction with 3×300 cm³ of AcOEt, washing with 2×70 cm³ of water, drying, filtering and evaporating. After chromatography on silica eluting with AcOEt-cyclo (3-7), impasting in essence G and drying, 3.72 g of product is obtained, 200 mg of which is recrystallized from MeOH-water (50-50). 149 mg of expected product is obtained.

IR Spectrum: in CHCl₃

═C—NH 3430–3225 cm⁻¹
═O 1682 cm⁻¹
Heterocycle 1522 cm⁻¹

Stage F ethyl 1-[(2'-((((dimethylamino) methylene) amino) sulphonyl) (1,1'-biphenyl) 4-yl) methyl]4-(methylthio) 2n-propylthio 1H-imidazole 5-carboxylate 1.04 g of the product obtained in Stage E above, 10 cm³ of DMF, 0.55 g of K₂CO₃, 2.1 g of 4'-(bromomethyl) N-[(dimethylamino) methylene](1,1'-biphenyl) 2-sulphonamide are mixed together at ambient temperature. Agitation is carried out at ambient temperature for 2 hours then the DMF is evaporated off, the residue is taken up in 3×150 cm³ of CH₂Cl₂, followed by washing with 2×50 cm³ of water, with 50 cm³ of a saturated solution of NaCl, drying, filtering and evaporating. Chromatography on silica is carried out eluting with AcOEt-cyclo (6-4), then crystallization from ether and 1.93 g of product is obtained, 100 mg of which is recrystallized from isopropyl ether. 66 mg of expected product is obtained. M.p.=160° C.

IR Spectrum: in CHCl₃

| | |
|---|---|
| ═O | 1685 cm⁻¹ |
| 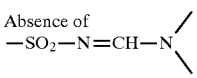SO₂N═CH—N⟨ | 1624 cm⁻¹ |

EXAMPLE 1

4'-((2-butyl 5-(2,4-dioxo 5-methyl 3-propyl 5-oxazolidinyl) 4-(methylthio) 1H-imidazol 1-yl) methyl) N-((propylamino) carbonyl) (1,1'-biphenyl) 2-sulphonamide Stage A ethyl 1-[(2'-(aminosulphonyl) (1,1'-biphenyl) 4-yl) methyl]2-butyl alpha-hydroxy alpha-methyl 4-(methylthio) 1H-imidazole 5-acetate 1.24 g of the product obtained in Preparation 1 is mixed with 30 cm³ of ethanol and 10 cm³ of concentrated HCl.

The solution obtained is heated under reflux for approximately two hours until total conversion.

The resultant product is by cooled down, diluted with water, alkalinized by the addition of NaOHc, the aqueous phase is saturated with K₂CO₃, extraction is carried out with ethyl acetate, then purification by chromatography on silica eluting with ethyl acetate. 930 mg of expected product (straw-coloured resin) is obtained.

IR Spectrum CHCl₃

| | |
|---|---|
| Absence of —SO₂—N═CH—N⟨ | |
| OH | ~3520 cm⁻¹ complex |
| NH₂ | ~3442 cm⁻¹, ~3355 cm⁻¹ |
| C═O | 1721 cm⁻¹ |
| Aromatic Heteroaromatic NH₂ | 1614–1592–1565–1543–1517 cm⁻¹ |

Stage B

4'-((2-butyl 5-(2,4-dioxo 5-methyl 3-propyl 5-oxazolidinyl) 4-(methylthio) 1H-imidazol 1-yl) methyl) N-((propylamino) carbonyl) (1,1'-biphenyl) 2-sulphonamide 300 mg of the product obtained in Stage A above is dissolved in 10 cm³ of acetone and 157 mg of K₂CO₃ is added. The reaction medium is heated under reflux then 0.13 cm³ of propyl isocyanate is introduced. Reflux is continued for approximately 1 hour, 0.5 cm³ of propyl isocyanate is added and heating under reflux is continued for approximately 1 hour. The K₂CO₃ is filtered out and the solvent and reagent are driven off at 60° C. 626 mg of product is obtained which is subjected to two purifications.

1) Purification by chromatography on silica with CH₂Cl₂ 60, AcOEt 40 and CHCl₃/MeOH 95/05 as solvent.

In this way 356 mg of product (colourless crystals) is recovered.

M.p.=178°–180° C.

2) Purification by recrystallization 356 mg of the product of chromatography obtained above is dissolved in 90 cm³ of iso ether and 10 cm³ of ethyl acetate under reflux. After hot filtering and concentrating to approximately 40 cm³, crystallization is started, followed by ice-cooling, filtering and drying at 50° C.

In this way 260 mg of expected product (colourless crystals) is obtained M.p.=170°–172° C.

IR Spectrum CHCl₃

Absence of OH

═C—NH— ~3416 and 3294 cm⁻¹

C=O 1812, 1737, 1713 cm$^{-1}$
Aromatic 1604, 1592, 1538, 1520 cm$^{-1}$
Heteroaromatic
Amide II

EXAMPLE 2 ethyl 2-methyl 4-(methylthio) 1-[(2'-(((( (phenylmethyl) amino) carbonyl) amino) sulphonyl) (1,1'-biphenyl) 4-yl) methyl]alpha-oxo 1H-imidazole 5-acetate Stage A ethyl 1-[(2'-(aminosulphonyl) (1,1'-biphenyl) 4-yl) methyl]2-methyl 4-(methylthio) alpha-oxo 1H-imidazole 5-acetate 4.8 g of the product obtained in preparation 2 is dissolved in a mixture of 50 cm$^3$ of ethanol and 30 cm$^3$ of concentrated HCl. The reaction medium is taken to reflux for approximately 5 hours. The solution is then concentrated under vacuum then taken up in ice-cooled water. Alkalinization is carried out by the addition of NH$_4$OH until pH ~8 then extraction is carried out with ethyl acetate, washing with water, drying then purifying by chromatography on silica eluting with ethyl acetate.

In this way 2.4 g of expected product is obtained.
IR Spectrum CHCl$_3$
—NH$_2$ 3443–3343 cm$^{-1}$
C=O 1734–1627 cm$^{-1}$
Aromatic 1593 cm$^{-1}$
Heteroatom 1565 cm$^{-1}$
NH$_2$ def. 1542 cm$^{-1}$ Stage B ethyl 2-methyl 4-(methylthio) 1-[(2'-(((( (phenylmethyl) amino) carbonyl) amino) sulphonyl) (1,1'-biphenyl) 4-yl) methyl]alpha-oxo 1H-imidazole 5-acetate 0.8 g of the product obtained in Stage A above is dissolved in 25 cm$^3$ of acetone and 465 mg of potassium carbonate is added. The medium is then taken to reflux, and 0.2 cm$^3$ of benzyl isocyanate is added dropwise, agitation is maintained under these conditions for approximately 1 hour. After evaporating to dryness, the residue is taken up in water then acidification is carried out by the addition of sodium hydrogen phosphate, the precipitate is separated off, washed abundantly with water then dried. Purification is carried out by impasting in a mixture of isopropanol 10 cm$^3$, isopropyl ether 20 cm$^3$, followed by separating, washing with 2×25 cm$^3$ of isopropyl ether and 480 mg of expected product (yellow solid) is obtained. M.p.=130° C.

IR Spectrum: CHCl$_3$
Absence of SO$_2$NH$_2$
complex —NH—C= 3395–3375 cm$^{-1}$
C=O 1732–1714–1624 cm$^{-1}$
Aromatic 1539–1497 cm$^{-1}$
Heteroatom
Amide II

EXAMPLE 3

2-methyl 4-(methylthio) alpha oxo-1-((2'-(((( (phenylmethyl) amino) carbonyl) amino) sulphonyl) (1,1'-biphenyl) 4-yl) methyl) 1H-imidazole 5-acetic acid 300 mg of the product obtained in Example 2 is introduced into a mixture of 15 cm$^3$ of ethanol and 0.1 cm$^3$ of KOH. Agitation is maintained overnight at ambient temperature. The suspension is then poured into water, then acidified to pH 2 by the addition of N hydrochloric acid, the white solid is finally separated off, washed abundantly with water then dried.

Purification

The crude product is impasted in 20 cm$^3$ of ethyl acetate, then in 10 cm$^3$ of boiling ethanol. After separating and washing with 10 cm$^3$ of ethanol, 85 mg of expected product (white solid) is obtained.

IR Spectrum: Nujol
Complex absorption OH/NH region
C=O 1720–1644–1630 cm$^{-1}$ sh.
Aromatic 1560 cm$^{-1}$
Heteroatom 1546 cm$^{-1}$
Amide II 1520–1497 cm$^{-1}$

|  | Microanalysis | | | |
| --- | --- | --- | --- | --- |
|  | C | H | N | S |
| % calculated | 58.11 | 4.52 | 9.68 | 11.08 |
| % found | 57.9 | 4.5 | 9.5 | 10.9 |

EXAMPLE 4 ethyl 4-(methylthio) alpha-oxo 1-[(2'-(((( (phenylmethyl) amino) carbonyl) amino) sulphonyl) (1,1'-biphenyl) 4-yl) methyl]2-propyl 1H-imidazole 5-acetate 3.6 g of the product obtained in Preparation 3 is introduced into 50 cm$^3$ of acetone then in one lot 2 g of potassium carbonate is added.

The medium is then taken to reflux and 1 cm$^3$ of benzyl isocyanate is added to it dropwise, reflux is maintained for approximately 2 hours.

The yellow suspension obtained is poured into 500 cm$^3$ of ice-cooled water then the medium is acidified by the addition of N hydrochloric acid, followed by separating, washing abundantly with water, then drying at 50° C. The crude product obtained is first purified by impasting in 50 cm$^3$ of isopropyl ether.

4.2 g of product is obtained (M.p.: 170° C.) 500 mg of which is recrystallized from 25 cm$^3$ of ethanol. After separating and drying, 300 mg of expected product is thus obtained.

M.p.: 188° C.
IR Spectrum CHCl$_3$
=C—NH 3375 cm$^{-1}$
C=O 1714 (F) 1621 cm$^{-1}$
Conjugated system 1537–1495 cm$^{-1}$
+aromatic
+Amide II

|  | Microanalysis | | | |
| --- | --- | --- | --- | --- |
|  | C | H | N | S |
| % calculated | 60.54 | 5.39 | 8.82 | 10.1 |
| % found | 60.5 | 5.3 | 8.7 | 10.0 |

EXAMPLE 5

4-(methylthio) 1-((2'-(((((phenylmethyl) amino) carbonyl) amino) sulphonyl) (1,1'-biphenyl) 4-yl) methyl) 2-propyl alpha oxo-1H-imidazole 5-acetic acid 5 cm$^3$ of 2N soda is added to 300 mg of the product obtained in Example 4, in suspension in 5 cm$^3$ of ethanol.

Agitation is maintained for approximately 1 hour at ambient temperature. The medium is acidified by the addition of 2N hydrochloric acid. The precipitation of a yellow solid is observed, this is separated out, washed abundantly with water then dried at 50° C.

The crude product obtained is taken up in 20 cm$^3$ of boiling ethanol, the white solid is separated out hot then washed with 2×10 cm$^3$ of ethanol. After drying at 50° C., 170 g of expected product is obtained. M.p.=215° C.

IR Spectrum: Nujol

General absorption OH/OH

+max absorption 3360–3350–3190 cm$^{-1}$

C=O 1720–1640–1610 cm$^{-1}$

Conjugated system 1558–1538–1510–1498 cm$^{-1}$

+Amide II

+Φ

| | Microanalysis | | | |
|---|---|---|---|---|
| | C | H | N | S |
| % calculated | 59.39 | 4.98 | 9.25 | 10.56 |
| % found | 59.2 | 4.9 | 9.4 | 10.4 |

EXAMPLE 6

S-methyl 2-butyl 1-[(2'-(((((cyclohexylmethyl) amino) carbonyl) amino) sulphonyl) (1,1'-biphenyl) 4-yl) methyl]4-(methylthio) alpha-oxo 1H-imidazole 5-ethanethioate 3.20 mg of the product obtained in Preparation 4 is introduced into 100 ml of anhydrous acetone and 1.78 g of potassium carbonate K$_2$CO$_3$. The whole is taken to reflux and 1.1 cm$^3$ of cyclohexylmethyl isocyanate is introduced. After agitation for about 1 hour, the solution is cooled down to ambient temperature, hydrolyzed with a saturated aqueous solution of NH$_4$Cl (150 ml) adjusted to pH ~4 using a 1N solution of HCl. Extracted is carried out three times with CH$_2$Cl$_2$, followed by drying, evaporating, then filtering on silica (eluant 50 CH$_2$Cl$_2$/50 AcOEt). In this way 3.5 g of expected product (yellow solid) is obtained. M.p.=145° C.

IR Spectrum CHCl$_3$

=C—NH 3406–3375 cm$^{-1}$

→=O 1716–1670–1616 cm$^{-1}$

Conjugated syst. 1598–1542–1492 cm$^{-1}$

+Aromatic

+Amide II

EXAMPLE 7

2-butyl 1-((2'-(((((cyclohexylmethyl) amino) carbonyl) amino) sulphonyl) (1,1'-biphenyl) 4-yl) methyl) 4-methylthio alpha oxo-1H-imidazole 5-acetic acid 2.8 g of the product obtained in Example 6 is introduced into 100 ml of ethanol. Then 15 ml of 2N NaOH is added at ambient temperature. The ethanol is then evaporated off and 50 ml of water is added. The aqueous phase is extracted three times with ether, then cooled down to 0° C. where it is acidified with 1N HCl. After filtering, drying and recrystallizing hot from anhydrous EtOH, 2 g of expected product is obtained.

| Microanalysis C$_{31}$H$_{38}$N$_4$O$_6$S$_2$, 1H$_2$O | | | | |
|---|---|---|---|---|
| | C | H | N | S |
| Calculated with 1 molecule of H$_2$O | 57.8 | 6.05 | 8.7 | 9.9 |
| Found | 58.0 | 5.9 | 8.6 | 9.9 |
| Calculated without molecule of H$_2$O | 59.42 | 6.07 | 8.95 | 10.22 |

EXAMPLE 8

4'-((2-butyl 5-((methylsulphinyl) acetyl) 4-(methylthio) 1H-imidazol 1-yl) methyl) N-((propylamino) carbonyl) (1,1'-biphenyl) 2-sulphonamide 3.52 g of NaH at 50% in oil is introduced, the NaH is removed form its oil by 3 successive washings with pentane, followed by drying. 42 cm$^3$ of anhydrous DMSO is added, the mixture is taken to 75° C., for approximately 1 hour, then the mixture is cooled down to 0° C. and 40 cm$^3$ of anhydrous THF is added to the DMSO anion formed then 12 g of ethyl 2-butyl H-(methylthio) 1-[[2'-((((propylamino) carbonyl) amino) sulphonyl) (1,1'-biphenyl) 4-yl]methyl]1H-imidazole 5-carboxylate, dissolved in 80 cm$^3$ of anhydrous THF, is added dropwise. The medium is left to rise to ambient temperature and is left under agitation for approximately 1 hour. Then the reaction mixture is poured into 400 cm$^3$ of distilled water and acidified to pH 2, with 2N hydrochloric acid, followed by extraction with 3×200 cm$^3$ of methylene chloride and the organic phase is washed with 1×200 cm$^3$ of a saturated solution of NH$_4$Cl and 2×200 cm$^3$ of distilled water.

The organic phase is dried, filtered and concentrated to dryness, followed by impasting in isopropyl ether then purifying on silica eluting with CH$_2$Cl$_2$-methanol (95-5), impasting in iso ether and 8.93 g of expected product (white powder) is obtained.

| | Microanalysis | | | | |
|---|---|---|---|---|---|
| | C | H | N | S | O |
| % calculated | 55.61 | 5.99 | 9.27 | 15.9 | 13.23 |
| % found | 55.5 | 5.9 | 9.2 | 16.0 | — |

IR Spectrum: CHCl$_3$

NH ~3370 cm$^{-1}$ associated

>=O 1710–1635 cm$^{-1}$

EXAMPLE 9

4'-((2-butyl 5-(2-(methylsulphinyl) acetyl) 4-(methylthio) 1H-imidazol 1-yl) methyl) N-(((phenylmethyl) amino) carbonyl) (1,1'-biphenyl) 2-sulphonamide 400 mg of the product obtained in Preparation 4 Stage A, 162 mg of K$_2$CO$_3$ and 10 cm$^3$ of anhydrous acetone are mixed together. The mixture is taken to reflux of the acetone and 0.156 ml of benzyl isocyanate is added to it dropwise. The reaction medium is left under agitation for approximately 1 hour, the acetone is evaporated off and the residue is taken up in NH$_4$Cl until a pH of 6–7 is obtained. Extraction is carried out with 3×50 cm$^3$ of CH$_2$Cl$_2$ and the extracts are washed with 2×50 cm$^3$ of water, then dried, filtered, and concentrated to dryness, followed by taking up in CH$_2$Cl$_2$ and purifying on silica eluting with CH$_2$Cl$_2$-methanol (93-7). 240 mg of expected product is collected.

IR Spectrum: CHCl$_3$
=C—NH— ~3375 cm$^{-1}$
>=O 1710–1637 cm$^{-1}$
Aromatic 1541–1498 cm$^{-1}$
+Amide II
>S→O 1044 cm$^{-1}$

EXAMPLE 10

2-butyl 4-(methylthio) alpha oxo 1-((2'-(((((phenylmethyl) amino) carbonyl) amino) sulphonyl) (1,1'-biphenyl) 4-yl) methyl) 1-H-imidazole 5-acetic acid Stage A 5-methyl 2-butyl 4-(methylthio) alpha oxo 1-[(2'-((((phenylmethyl) amino) carbonyl) amino) sulphonyl) (1,1'-biphenyl) 4-yl) methyl]1-H-imidazole 5-ethanethioate 1.4 g of the product obtained in Preparation 4 is introduced into 560 mg of K$_2$CO$_3$, dissolved in 35 cm$^3$ of acetone, the mixture is taken to reflux of the acetone and 500 μl of benzyl isocyanate is added to it. It is left under agitation for approximately ½ hour, the acetone is evaporated off, the residue is taken up in 30 cm$^3$ of water which is adjusted to pH 6–7 using a saturated solution of ammonium chloride. The aqueous phase is extracted with 3×50 cm$^3$ of methylene chloride and the organic phase is washed with 2×50 cm$^3$ of distilled water, then dried, filtered and concentrated to dryness. After impasting in ethyl ether, 1.67 g of a yellow powder is obtained which is recrystallized from 50 cm$^3$ of hot ethyl acetate, filtered, concentrated to a minimum amount of ethyl acetate and left to crystallize at ambient temperature. The crystals are separated out and dried. 1.02 g of expected product (yellow crystals) is obtained. M.p.=145° C.

Stage B 2-butyl 4-(methylthio) alpha oxo 1-((2'-(((((phenylmethyl) amino) carbonyl) amino) sulphonyl) (1,1'-biphenyl) 4-yl) methyl) 1-H-imidazole 5-acetic acid 990 mg of the product obtained in Stage A above, dissolved in 20 cm$^3$ of ethanol and 20 cm$^3$ of 2N NaOH is introduced. The reaction medium is left under agitation at ambient temperature for approximately ¼ hour, then the ethanol is evaporated off and the residue is taken up in 50 cm$^3$ of distilled water, the solution is acidified to pH 6–7 with 2N HCl. The precipitate formed is separated off, washed with distilled water then dried at 80° C., purified by dissolving it hot in the minimum amount of ethanol, filtering and leaving to recrystallize at ambient temperature. The crystals are separated out and dried and 473 mg of expected product is obtained. M.p.=208° C.

IR Spectrum: Nujol
>=O 1720–1620 cm$^{-1}$
Aromatic 1542–1595–1495 cm$^{-1}$
Heteroaromatic
Amide II

EXAMPLE 11

2-butyl 4-(methylthio) alpha oxo N-(phenylmethyl) 1-((2'-(((((phenylmethyl) amino) carbonyl) amino) sulphonyl) (1,1'-biphenyl) 4-yl) methyl) 1-H-imidazole 5-acetamide Stage A 1-[(2'-(aminosulphonyl) (1,1'-biphenyl) 4-yl) methyl]2-butyl 4-(methylthio alpha-oxo N-(phenylmethyl) 1H-imidazole 5-acetamide 503 mg of the product obtained in Preparation 4, 530 μl of >99% benzylamine and 6 cm$^3$ of toluene are mixed together. The mixture is taken to reflux of toluene under agitation for approximately 15 minutes, then the toluene is evaporated off. The residue is taken up in 50 cm$^3$ of ethyl acetate and this organic phase is washed with 2×50 cm$^3$ of distilled water, 1×50 cm$^3$ of saturated NaCl, followed by drying, filtering and concentrating to dryness. Purification is carried out on silica eluting with ethyl acetate-cyclohexane (1-1), and 410 mg of expected product (yellow foam) is collected.

IR Spectrum: CHCl$_3$
NH/NH$_2$ 3425 cm$^{-1}$ complex
3345 cm$^{-1}$
>=O 1682–1614 cm$^{-1}$
Conj. system
+Aromatic 1526–1498 cm$^{-1}$
+Amide II
+NH$_2$ dif.

Stage B 2-butyl 4-(methylthio) alpha oxo N-(phenylmethyl) 1-((2'-(((((phenylmethyl) amino) carbonyl) amino) sulphonyl) (1,1'-biphenyl) 4-yl) methyl) 1-H-imidazole 5-acetamide 380 mg of the product obtained in Stage A above, 182 mg of K$_2$CO$_3$ are introduced and dissolved in 10 cm$^3$ of acetone. The reaction medium is taken to reflux of acetone and 88 μl of 99% benzyl isocyanate is added. The whole is left under agitation for approximately 1 hour. The acetone is then evaporated off and the residue is taken up in 50 cm$^3$ of methylene chloride and washed with 1×20 cm$^3$ of a saturated solution of NH$_4$Cl, 1×20 cm$^3$ of distilled water. The organic phase is dried, filtered and concentrated to dryness.

After impasting in cyclohexane, separation and drying are carried out, followed by purifying by dissolving hot in the minimum amount of methanol, filtering and concentrating, then leaving to crystallize at ambient temperature and 75 mg of expected product is collected. M.p.=194° C.

IR Spectrum: CHCl$_3$
=C—NH— ~3390 cm$^{-1}$
>=O 1713–1665–1623 cm$^{-1}$
Amide II 1535–1497 cm$^{-1}$
Aromatic
Heteroaromatic

EXAMPLE 12 ethyl 2-butyl 4-(methylthio) beta oxo 1-((2'-(((( (propylamino) carbonyl) amino) sulphonyl) (1,1'-biphenyl) 4-yl) methyl) 1-H-imidazole 5-propanoate Stage A Preparation of ethyl and potassium malonate

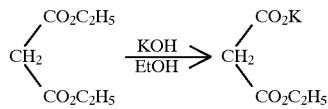

According to the method described by Strube R. E. (Organic Syntheses Coll. Vol IV. 1963, 417) modified by G. Bram and M. Viekas (Bull. Soc. Chim. 1964, 945), 80 g of ethyl malonate is dissolved in 50 ml of ethanol 100 and cooled down. Then a cold solution of 28 g of potash in 200 ml of ethanol 100 is added dropwise over approximately two hours. Then the reaction medium is left under agitation overnight.

Then the precipitate is separated out, rinsed with ether, dried and 61 g of the expected potassium salt (white crystals) is obtained.

Stage B

Preparation of the acid chloride 2.2 ml of redistilled thionyl chloride is added to a suspension of 1.088 g of 2-butyl H-(methylthio) 1-[[2'-((( (propylamino) carbonyl) amino) sulphonyl) (1,1'-biphenyl) 4-yl]methyl]1H-imidazole 5-carboxylic acid, prepared as indicated in EP 0,503,162, in 44 ml of anhydrous toluene.

Agitation is carried out for approximately one hour at ambient temperature, then overnight at 55° C. Then the excess toluene and thionyl chloride are evaporated off, the residue is taken up in 30 ml of toluene and evaporated again (3 times) then dried for approximately 2 hours at 50° C.

Stage C

Condensation 714 mg of product obtained in Stage A above is introduced into 12 ml of ethyl acetate. After cooling down to approximately 4° or 5° C., 1.062 g of triethylamine then 656 mg of anhydrous magnesium chloride are added.

The mixture is then taken gradually to 35° C. (±1° C.) and maintained at this temperature for approximately 6 hours under agitation.

The reaction medium is again cooled down to approximately 2° C. then the acid chloride obtained in Stage B above in 20 ml of anhydrous THF is added over approximately 25 minutes. After rinsing with 2 times 3 ml of anhydrous THF the reaction medium is allowed to return to ambient temperature then left under agitation overnight.

The reaction medium is cooled down to a temperature lower than 5° C. then 14 ml of N HCl is added dropwise, followed by decanting, reextracting with ethyl acetate 3 times, washing with water and salt water, drying and the solvents are evaporated off.

Purification is carried out on silica eluting with $CH_2Cl_2$-ethyl acetate (8-2)+0.5% methanol and 757 mg of expected product is obtained. M.p. 193°–195° C.

IR Spectrum: $CHCl_3$

=C—NH— 3375 cm$^{-1}$ complex

>=O 1730–1706 cm$^{-1}$ 1632 cm$^{-1}$ (conjugated ketone)

Amide II 1540 cm$^{-1}$

EXAMPLE 13

2-butyl 4-(methylthio) 1-((2'-((((propylamino) carbonyl) amino) sulphonyl) (1,1'-biphenyl) 4-yl) methyl) N-(1H-tetrazol 5-yl) 1H-imidazole 5-carboxamide 900 mg of 2-butyl H-(methylthio) 1-[[2'-((((propylamino) carbonyl) amino) sulphonyl) (1,1'-biphenyl) 4-yl]methyl] 1H-imidazole 5-carboxylic acid, described in EP 0503162, recrystallized from isopropanol is introduced then suspended in 10 ml of toluene. 1 ml thionyl chloride $SOCl_2$ is added and agitation is carried out for 1 hour at ambient temperature, then for 15 hours at 55° C. Then the solvent is evaporated off. The residue is taken up several times in toluene to eliminate all the $SOCl_2$.

The resultant product is suspended in 3 ml of anhydrous THF and a 20 ml solution of anhydrous THF containing 510 mg of aminotetrazole hydrate (commercial) and 210 μl of pyridine is added then agitation is carried out for approximately 20 hours at ambient temperature. Then the solution is hydrolyzed with a saturated solution of $NH_4Cl$ and extracted with $CH_2Cl_2$, followed by drying, evaporating and purifying by chromatography on silica eluting with $CH_2Cl_2$ 10% MeOH, then with 50 AcOEt/45 Acetone/5 $CH_2Cl_2$ and MeOH is added progressively until it represents 10% of the eluant.

After filtering and drying 180 mg of expected product (white solid) is obtained. M.p.=130° C.

IR Spectrum: $CHCl_3$

OH—NH region strong absorption with NH

>=O 1697–1640 cm$^{-1}$

Amide II 1570 cm$^{-1}$

C=N $NH_2$

EXAMPLE 14 ethyl 4-(methylthio) 1-((2'-((((propylamino) carbonyl) amino) sulphonyl) (1,1'-biphenyl) 4-yl) methyl) 2-(propylthio) 1H-imidazole 5-carboxylate Stage A ethyl 4-(methylthio) 1-((2'-sulphonamide (1,1'-biphenyl) 4-yl) methyl) 2-(propylthio) 1H-imidazole 5-carboxylate 5.49 g of the product obtained in Preparation 6, 100 cm$^3$ of EtOH and 50 cm$^3$ of fuming 37% HCl are introduced. The reaction medium is heated under reflux for 1 hour, the medium is alkalinized with 32% soda, the EtOH is evaporated off, extraction is carried out with 3×300 cm$^3$ of $CH_2Cl_2$, followed by washing with 2×30 cm$^3$ of water, drying and filtering. After chromatography on silica eluting with AcOEt-cyclo (3-7), then crystallization from ether, separating and washing eith ether, 2.32 g of expected product is obtained. M.p.=113° C.

IR Spectrum: $CHCl_3$ $SO_2NH_2$ 3440–3340 cm$^{-1}$

>=O 1686 cm$^{-1}$

Stage B ethyl 4-(methylthio) 1-((2'-((((propylamino) carbonyl) amino) sulphonyl) (1,1'-biphenyl) 4-yl) methyl) 2-(propylthio) 1H-imidazole 5-carboxylate 200 mg of the product obtained in Stage A above, 4 cm$^3$ of acetone and 109 mg of $K_2CO_3$ are introduced at ambient temperature. The reaction medium is heated to reflux and 0.06 cm³ of propyl isocyanate is introduced, followed by agitation under reflux for approximately 15 minutes. TLC eluant AcOEt-CH$_2$Cl$_2$ (3-7) UV.

Approximately 5 cm³ of a saturated solution of NH$_4^+$Cl$^-$ and 10 cm³ of water are added, followed by extraction with 2×50 cm³ of CH$_2$Cl$_2$, washing with 2×20 cm³ of water, drying, filtering, evaporating, dissolving in approximately 20 cm³ of ether, hot filtering, concentrating to approximately 3 cm³, leaving to crystallize at ambient temperature, separating with ether and drying at ambient temperature. After recrystallizing form ether 107 mg of expected product is obtained. M.p.=148° C.

IR Spectrum: CHCl$_3$
=C—NH 3404–3365 cm$^{-1}$
>=O 1710–1685 cm$^{-1}$
Conjugated system+1614–1592–1538–1500 cm$^{-1}$
Aromatic+
Amide II+

EXAMPLE 15

4-(methylthio) 1-((2'-(((((phenylmethyl) amino) carbonyl) amino) sulphonyl) (1,1'-biphenyl) 4-yl) methyl) 2-propyl N-(2H-tetrazol 5-yl) 1H-imidazole 5-carboxamide Stage A ethyl 4-(methylthio) 1-[(2'-(((((phenylmethyl) amino) carbonyl) amino) sulphonyl) (1,1'-biphenyl) 4-yl) methyl]2-propyl 1H-imidazole 5-carboxylate 2 g of the product obtained in Preparation 5, dissolved in 25 ml of anhydrous acetone and 1.2 g of potassium carbonate are introduced. The reaction medium is taken to reflux and 740 µl of benzylisocyanate is added. After agitation for approximately 2 hours, the reaction medium is cooled down to ambient temperature, hydrolyzed with a saturated aqueous solution of NH$_4$Cl then extraction is carried out with methylene chloride. After drying, recrystallizing from ether and filtering, 1.9 g of expected product is obtained.

Stage B 4-(methylthio) 1-[(2'-(((((phenylmethyl) amino) carbonyl) amino) sulphonyl) (1,1'-biphenyl) 4-yl) methyl]2-propyl 1H-imidazole 5-carboxylic acid 1.8 g of the product obtained in Stage A above, in 10 ml of ethanol and 10 ml of 2N soda is introduced then left under agitation at ambient temperature for approximately 36 hours. Then the ethanol is evaporated off and, after adding 25 ml of water, the aqueous phase is extracted with ether, then filtered, ice-cooled down to 0° C. and slowly acidified with 1N HCl until a pH of 1.5 is obtained. After filtering and drying 1.4 g of expected product is obtained.

IR Spectrum: CHCl$_3$
Acid according to the OH region
=C—NH 3480 cm$^{-1}$
>=O 1706–1690 cm$^{-1}$ complex
Aromatic 1539–1521–1500 cm$^{-1}$
Heteroaromatic
Amide II Stage C 4-(methylthio) 1-((2'-(((((phenylmethyl) amino) carbonyl) amino) sulphonyl) (1,1'-biphenyl) 4-yl) methyl) 2-propyl N-(2H-tetrazol 5-yl) 1H-imidazole 5-carboxamide 270 mg of the product obtained in Stage B above in 5 ml of toluene and 300 µl of SOCl$_2$ (thionyl chloride) is introduced then subjected to agitation for approximately 1 hour at ambient temperature, then for approximately 15 hours at 55° C. Then the solvent is evaporated off, the SOCl$_2$ is eliminated under vacuum. The acid chloride obtained is suspended in 3 ml of anhydrous THF then a 10 ml solution of anhydrous THF is added, containing 150 mg of aminotetrazole and 150 µl of pyridine is added. Agitation is carried out for approximately 20 hours at ambient temperature. The solution is then hydrolyzed with a saturated aqueous solution of NH$_4$Cl and extraction is carried out 3 times with CH$_2$Cl$_2$. After drying and evaporating the solvent, separation of the sought amide of the starting acid is carried out by preparative reversed-phase HPLC eluting with MeOH—H$_2$O (60-40) with NH$_4^+$ ACO$^-$ 0.05M. The product is recrystallized from MeOH. In this way 70 mg of expected product is collected.

M.p.=228° C.
NMR (DMSO)
0.98 (t) CH$_3$
1.69 (m) CH$_2$
2.75 (m) CH$_2$-Im
2.46 (s) SMe
4.0 (d, s after HNCH$_2$PH exchange)
5.53 (s) NCH$_2$PH
6.82 (2H)
7.04 (2H)
7.17 (7 to 8H)
7.56 (m) 2H
8.04 (dd) 1H
MS (SIMS)
MH$^+$=646.

EXAMPLE 16

2-butyl 1-((2'-(((((cyclohexylmethyl) amino) carbonyl) amino) sulphonyl) (1,1'-biphenyl) 4-yl) methyl) 4-(methylthio) alpha-oxo 1H-imidazole 5-acetamide 250 mg of the product of Example 6 is introduced into 5 ml of anhydrous EtOH and 90 mg of ammonium acetate NH$_4$OAc. The reaction medium is taken to reflux overnight, hydrolyzed with an aqueous solution of NH$_4$Cl and extracted with AcOEt. After drying and evaporating, purification is carried out on silica eluting with AcOEt-CH$_2$Cl$_2$ (50-50) then recrystallization from CH$_2$Cl$_2$ and a minimum amount of iso ether and 65 mg of expected product is obtained.

IR Spectrum: CHCl$_3$
NH/NH$_2$ 3510–3400 cm$^{-1}$
>=O 1708–1690–1622 cm$^{-1}$
Conjugated system 1560–1552–1490 cm$^{-1}$
Aromatic
NH, NH$_2$

EXAMPLE 17

2-butyl 1-((2'-(((((cyclohexylmethyl) amino) carbonyl) amino) sulphonyl) (1,1'-biphenyl) 4-yl) methyl) alpha-((2,4-dinitrophenyl) hydrazono) 4-(methylthio) 1H-imidazole 5-acetic acid The operation is carried out as in Example 16, by introducing 250 mg of the product of Example 7, in 10 ml of absolute ethanol and 150 mg of 2,4-dinitrophenylhydrazine. The reaction medium is heated under reflux for approximately 5 hours under agitation, and 160 mg of expected product is obtained. M.p.=254° C.

IR Spectrum: Nujol
General absorption OH/NH
>=O 1706–1668–1652 cm$^{-1}$
C=N
Conjugated system+1618–1590–1518–1501 cm$^{-1}$
Aromatic+
Amide II+
NO$_2$

EXAMPLE 18

2-butyl alpha-((2,4-dinitrophenyl) hydrazono) 4-(methylthio) 1-((2'-(((((phenylmethyl) amino) carbonyl) amino) sulphonyl) (1,1'-biphenyl) 4-yl) methyl) 1H-imidazole 5-acetic acid 100 mg of the product of Example 10 is introduced into 5 ml of EtOH and 48 mg of 2,4-dinitrophenylhydrazine. The reaction medium is heated under reflux for approximately 6 hours under agitation, then cooled down, filtered and 50 mg of expected product is obtained. M.p.=252° C.

| Microanalysis: C$_{37}$H$_{36}$N$_8$O$_9$S$_2$, M = 543 | | | | |
|---|---|---|---|---|
| | C | H | N | S |
| % calculated | 55.5 | 4.5 | 14.0 | 8.0 |
| % found | 55.3 | 4.3 | 13.7 | 8.3 |

EXAMPLE 19

4-(methylthio) 1-((2'-(((((propylamino) carbonyl) amino) sulphonyl) (1,1'-biphenyl) 4-yl) methyl) 2-(propylthio) 1H-imidazole 5-carboxylic acid 300 mg of the product of Example 14, 10 cm$^3$ of THF, 2 cm$^3$ of 2N NaOH and 8 cm$^3$ of water are introduced at ambient temperature, then agitation is carried out at ambient temperature for 24 hours.

The THF is evaporated off, 10 cm$^3$ of water is added, acidification to ph 5–6 is carried out with acetic acid, followed by extraction with 3×80 cm$^3$ of CH$_2$Cl$_2$, drying, filtering and evaporating. Crystallization is carried out from 20 cm$^3$ of AcOEt, 5 cm$^3$ of MeOH (hot, approximately 40° C.), followed by filtering, concentrating to approximately 10 cm$^3$, leaving to crystallize, separating, washing with AcOEt then with ether and drying at ambient temperature. 183 mg of expected product is obtained. M.p.=195° C.

IR Spectrum: Nujol
OH/NH region max. 3340 cm$^{-1}$+general absorption
>=O 1664 cm$^{-1}$ complex
Aromatic 1592–1552–1504–1483 cm$^{-1}$
Heteroaromatic
Amide II+

EXAMPLE 20

4'-((4-(methylthio) 5-(2-(phenylsulphinyl) acetyl) 2-propyl 1H-imidazol-1-yl) methyl) N-(((phenylmethyl) amino) carbonyl) (1,1'-biphenyl) 2-sulphonamide 203 mg of phenylmethylsulphoxide and 440 mg of the ester obtained as in Example 15 Stage A are cooled down to 0° C. 3.6 cm$^3$ of lithium bis (trimethylsilyl) amide is added over 1 minute. Agitation is carried out for 15 minutes at 0° C., the reaction medium is left to return to ambient temperature, maintained for 15 minutes, 10 cm$^3$ of a saturated aqueous solution of ammonium chloride is added, N hydrochloric acid is added until the pH equals ⅔ then extraction is carried out with ethyl acetate. The organic extracts are washed with water, dried and the solvent is evaporated off. After chromatographing the residue on silica (eluant: CH$_2$Cl$_2$—MeOH 90-10), 356 mg of crude product is obtained which is solubilized in methylene chloride then isopropyl ether is added, the reaction medium is cooled down to −78° C., the precipitate is dissolved in hot acetonitrile and 250 mg of crystallized expected product is collected.

IR Spectrum: CHCl$_3$
NH 3300 cm$^{-1}$
C=O 1708–1636 cm$^{-1}$
Conjugated system
Aromatic 1587–1540–1497 cm$^{-1}$
amide II
S→O 1038 cm$^{-1}$ By operating as in Example 15 Stages B and C or in Example starting with the product obtained in Example 15A (or analogues prepared in an identical manner) and the appropriate reagents, the following products were prepared:

EXAMPLE 21 ethyl 2-butyl 4-(methylthio) beta-oxo-1-((2'-((((phenylmethyl) amino) carbonyl) amino) sulphonyl) (1,1'-biphenyl) 4-yl) methyl) 1H-imidazole 5-propanoate M.p.=173°–175° C.
rf=0.35 (CH$_2$Cl$_2$-AcOEt).

EXAMPLE 22 methyl 2-butyl 4-(methylthio) beta-oxo-1-((2'-((((phenylmethyl) amino) carbonyl) amino) sulphonyl) (1,1'-biphenyl) 4-yl) methyl) 1H-imidazole 5-propanoate M.p.=170° C.
rf#0.85 (CH$_2$Cl$_2$—MeOH 90-10).

EXAMPLE 23 methyl 2-butyl 1-((2'-(((((cyclohexylmethyl) amino) carbonyl) amino) sulphonyl) (1,1'-biphenyl) 4-yl) methyl) 4-(methylthio) beta-oxo 1H-imidazole 5-propanoate M.p.≃110° C.
rf #0.67 (CH$_2$Cl$_2$—MeOH 90-10).

EXAMPLE 24

4'-((2-butyl 4-(methylthio) 5-(3-phenyl 1,3-dioxopropyl) 1H-imidazol 1-yl) methyl) N-(((phenylmethyl) amino) carbonyl) (1,1'-biphenyl) 2-sulphonamide M.p.=180° C.
rf=0.4 (CH$_2$Cl$_2$—MeOH 97-3).

EXAMPLE 25

4'-((4-((difluoromethyl) thio) 5-((phenylsulphinyl) acetyl) 2-propyl 1H-imidazol 1-yl) methyl) N-(((phenylmethyl) amino) carbonyl) (1,1'-biphenyl) 2-sulphonamide.

M.p.≃103° C.
rf=0.25 (AcOEt-cyclohexane 8-2).

EXAMPLE 26

4-(methylthio) 1-((2'-(((((phenylmethyl) amino) carbonyl) amino) sulphonyl) (1,1'-biphenyl) 4-yl) methyl) 2-propyl 1H-imidazole 5-carboxamide M.p.=112° C.

EXAMPLE 27

2-butyl 4-(methylthio) 1-((2'-((((propylamino) carbonyl) amino) sulphonyl) (1,1'-biphenyl) 4-yl) methyl) 1H-imidazole 5-carboxamide M.p.≃90° C.
rf=0.45 (AcOEt).

EXAMPLE 28

4'-((5-2-(methylsulphinyl acetyl) 4-(methylthio) 2-propyl 1H-imidazol 1-yl) methyl) N-(( (phenylmethyl) amino) carbonyl) (1,1'-biphenyl) 2-sulphonamide M.p.=100° C.
rf=0.5 (CH$_2$Cl$_2$—MeOH 95-5).

EXAMPLE 29

4'-((2-butyl 4-(methylthio) 5-((phenylsulphonyl) acetyl) 1H-imidazol 1-yl) methyl) N-(( (phenylmethyl) amino) carbonyl) (1,1'-biphenyl) 2-sulphonamide M.p.=185° C.

EXAMPLE 30

4'-((5-(((4-methoxyphenyl) sulphonyl) acetyl) 4-(methylthio) 2-propyl 1H-imidazol-1-yl) methyl) N-(((phenylmethyl) amino) carbonyl) (1,1'-biphenyl) 2-sulphonamide M.p.=158° C.

EXAMPLE 31

4'-((5-(((4-methylphenyl) sulphinyl) acetyl) 4-(methylthio) 2-propyl 1H-imidazol-1-yl) methyl) N-(((phenylmethyl) amino) carbonyl) (1,1'-biphenyl) 2-sulphonamide M.p.≃115° C.

EXAMPLE 32

(S) 4'-((5-(((4-methylphenyl) sulphinyl) acetyl) 4-(methylthio) 2-propyl 1H-imidazol-1-yl) methyl) N-(((phenylmethyl) amino) carbonyl) (1,1'-biphenyl) 2-sulphonamide M.p.=109° C. (c=0.5 CHCl$_3$).
rf=0.40 (AcOEt-hexane 80-20).

EXAMPLE 33

4'-((5-(cyanoacetyl) 4-(methylthio) 2-propyl 1H-imidazol-1-yl) methyl) N-(((phenylmethyl) amino) carbonyl) (1,1'-biphenyl) 2-sulphonamide M.p.=190°–193° C.
rf=0.20 (AcOEt-hexane 60-40).

EXAMPLE 34

4'-((4-(methylthio) 5-((phenylsulphinyl) acetyl) 2-propyl 1H-imidazol-1-yl) methyl) N-(((2-thienylmethyl) amino) carbonyl) (1,1'-biphenyl) 2-sulphonamide M.p.=200° C.
rf=0.37 (CH$_2$Cl$_2$-AcOEt 60-40).

EXAMPLE 35

4'-((2-butyl 5-(2-(methylsulphonyl) acetyl) 4-(methylthio) 1H-imidazol-1-yl) methyl) N-( (propylamino) carbonyl) (1,1'-biphenyl) 2-sulphonamide M.p.=159° C.
rf=0.17 (CH$_2$Cl$_2$-AcOEt 80-20).

EXAMPLE 36

4'-((2-butyl 4-(methylthio) 5-(2-(phenylsulphinyl) acetyl) 1H-imidazol-1-yl) methyl) N-(( (phenylmethyl) amino) carbonyl) (1,1'-biphenyl) 2-sulphonamide M.p.=130° C.

EXAMPLE 37

4'-((2-butyl 5-(2-(methylsulphonyl) acetyl) 4-(methylthio) 1H-imidazol-1-yl) methyl) N-(( (phenylmethyl) amino) carbonyl) (1,1'-biphenyl) 2-sulphonamide M.p.=116° C.
rf=0.43 (CH$_2$Cl$_2$—MeOH 96-4).

EXAMPLE 38

4'-((2-butyl 5-((1-((4-methoxyphenyl) methyl) 1H-tetrazol-5-yl) acetyl) 4-(methylthio) 1H-imidazol 1-yl) methyl) N-(((phenylmethyl) amino) carbonyl) (1,1'-biphenyl) 2-sulphonamide M.p.=185° C.
rf=0.25 (CH$_2$Cl$_2$—MeOH 97-3).

EXAMPLE 39

4'-((2-butyl 5-((4-methoxyphenyl) (5-methyl) 2H-tetrazol-2-yl) acetyl) 4-(methylthio) 1H-imidazol 1-yl) methyl) N-(((phenylmethyl) amino) carbonyl) (1,1'-biphenyl) 2-sulphonamide M.p.=215° C.
rf=0.38 (CH$_2$Cl$_2$-AcOEt 70-30).

EXAMPLE 40

4'-((2-butyl 4-(methylthio) 5-(2-phenylsulphonyl) acetyl) 1H-imidazol 1-yl) methyl) N-(( (phenylmethyl) amino) carbonyl) (1,1'-biphenyl) 2-sulphonamide M.p.=191° C.
rf=0.16 (AcOEt-cyclohexane 5-5).

EXAMPLE 41

4'-((2-butyl 5-(2-((4-fluorophenyl) sulphonyl) acetyl) 4-(methylthio) 1H-imidazol 1-yl) methyl) N-(((phenylmethyl) amino) carbonyl) (1,1'-biphenyl) 2-sulphonamide M.p.=129° C.
rf=0.3 (AcOEt-cyclohexane 5-5).

EXAMPLE 42

4'-((2-butyl 4-((difluoromethyl) thio) 5-(
(phenylsulphinyl) acetyl) 1H-imidazol 1-yl) methyl)
N-(((phenylmethyl) amino) carbonyl) (1,1'-
biphenyl) 2-sulphonamide M.p.≃95°–100° C.

EXAMPLE 43

4'-((2-butyl 4-((difluoromethyl) thio) 5-(
(phenylsulphonyl) acetyl) 1H-imidazol 1-yl)
methyl) N-(((phenylmethyl) amino) carbonyl) (1,1'-
biphenyl) 2-sulphonamide M.p.≃190° C.

EXAMPLE 44

4'-((2-ethyl 5-((methylsulphonyl) acetyl) 4-
methylthio) 1H-imidazol 1-yl) methyl) N-((
(phenylmethyl) amino) carbonyl) (1,1'-biphenyl) 2-
sulphonamide M.p.=180° C.
rf#0.37 (CH$_2$Cl$_2$-AcOEt-MeOH 6-4-0.5).

EXAMPLE 45

4'-((2-ethyl 4-(methylthio) 5-((phenylsulphinyl)
acetyl) 1H-imidazol 1-yl) methyl) N-((
(phenylmethyl) amino) carbonyl) (1,1'-biphenyl) 2-
sulphonamide M.p.=228° C.
rf#0.3 (AcOEt-hexane 80-20).

EXAMPLE 46

(±) N-(((cyclopentylmethyl) amino) carbonyl) 4'-(
(4-(methylthio) 5-((phenylsulphinyl) acetyl) 2-
propyl 1H-imidazol 1-yl) methyl) (1,1'-biphenyl) 2-
sulphonamide M.p.≃106° C.
rf=0.5 (CH$_2$Cl$_2$-AcOEt 6-4).

EXAMPLE 47

(±) N-(4'-((4-(methylthio) 5-((phenylsulphinyl)
acetyl) 2-propyl 1H-imidazol 1-yl) methyl) (1,1'-
biphenyl-2yl) sulphonyl) cyclopentanepropanamide M.p.≃95° C.
rf=0.7 (CH$_2$Cl$_2$-AcOEt 6-4).

EXAMPLE 48

(±) N-(((cyclohexylmethyl) amino) carbonyl) 4'-((4-
(methylthio) 5-((phenylsulphinyl) acetyl) 2-propyl
1H-imidazol 1-yl) methyl) (1,1'-biphenyl) 2-
sulphonamide M.p.≃90°/95° C.
rf=0.4 (CH$_2$Cl$_2$-AcOEt 8-2).

EXAMPLE 49

4'-((5-acetyl 2-butyl 4-(methylthio) 1H-imidazol 1-
yl) methyl) N-(((cyclohexylmethyl) amino)
carbonyl) (1,1'-biphenyl) 2-sulphonamide a) Alkylation of the ester.

By operating as in Example 20 starting with ethyl 1-((2'-
(aminosulphonyl 1,1'-biphenyl) 4-yl) methyl)
4-(methylthio) 2-butyl 1H-imidazol 5-carboxylate prepared
as indicated in Preparation 5 for the analogue 2-propyl of
lithium bis (trimethylsilyl) amide and dimethylsulphoxide,
the sulphoxide derivative is obtained with a 70% yield.

b) Desulphurization.

220 mg of zinc and a solution of 7 cm$^3$ of ammonium
chloride and 10 cm$^3$ of ethanol are added to 300 mg of
product obtained in the preceding stage. Agitation is carried
out for 48 hours at ambient temperature; followed by
filtering, washing with ethyl acetate, extracting with methylene chloride, evaporating the solvent off under reduced
pressure and the acyl derivative is collected with an 80%
yield.

c) Condensation.

The product obtained in the preceding stage is heated for
one hour at reflux temperature with 2 equivalents of potassium carbonate and 1.2 equivalents of cyclohexylmethylisocyanate in acetone. The reaction medium is left to return
to ambient temperature, the solvent is evaporated off, the
residue is taken up in dichloromethane, washed with an
aqueous solution of N hydrochloric acid, dried and concentrated under reduced pressure. After recrystallization from
ethanol, the expected product is obtained with a yield of
60%.

M.p.=166° C.

By operating as in Example 1 Stage B or Example 49
Stage C using the appropriate acyl derivative and the appropriate isocyanate, the following products were prepared:

EXAMPLE 50

2-butyl 4'-((4-methylthio) 5-((1H-tetrazol 5-yl)
carbonyl) 1H-imidazol 1-yl) methyl) N-((
(phenylmethyl) amino) carbonyl) (1,1'-biphenyl) 2-
sulphonamide rf=0.3 (CH$_2$Cl$_2$—MeOH 80-20).

EXAMPLE 51

N-(((cyclohexylmethyl) amino) carbonyl) 4'-((2-
ethylthio) 5-(2-(methylsulphinyl) acetyl) 4-
(methylthio) 1H-imidazol 1-yl) methyl) (1,1'-
biphenyl) 2-sulphonamide M.p.≃180° C.

EXAMPLE 52

2-butyl 4-(methylthio) N-pentyl 1-((2'-((((
(phenylmethyl) amino) carbonyl) amino) sulphonyl)
(1,1'-biphenyl) 4-yl) methyl) 1H-imidazol 5-
carboxamide M.p.=138° C.
rf=0.25 (AcOEt-cyclohexane 5-5).

EXAMPLE 53

4'-((2-butyl 4-(methylthio) 5-(1-oxo 2-
(phenylsulphonyl) pentyl 1H-imidazol-1-yl) methyl)
N-(((phenylmethyl) amino) carbonyl) (1,1'-
biphenyl) 2-sulphonamide M.p.=162° C.
rf=0.34 (AcOEt-cyclohexane 5-5).

EXAMPLE 54

4'-((2-butyl 4-(methylthio) 5-((1,1-dioxydo
tetrahydro 2-thienyl) carbonyl) 1H-imidazol-1-yl)
methyl) N-(((phenylmethyl) amino) carbonyl) (1,1'-
biphenyl) 2-sulphonamide rf=0.23 (CH$_2$Cl$_2$-AcOEt 85-15).

EXAMPLE 55

2-ethyl 4-(methylthio) 1-((2'-(((((phenylmethyl) amino) carbonyl) amino) sulphonyl) (1,1'-biphenyl) 4-yl) methyl) 1H-imidazol 5-carboxamide M.p.=140° C.

rf #0.22 (AcOEt-CH$_2$Cl$_2$—MeOH 6-4-0.5).

EXAMPLE 56 ethyl 2-butyl 4-(methylthio) beta-oxo 1-((2'-((( (phenylmethoxy) carbonyl) amino) sulphonyl) (1,1'-biphenyl) 4-yl) methyl) 1H-imidazol 5-propanoate (potassium salt)

M.p.=130° C.

rf #0.5 (CH$_2$Cl$_2$-AcOEt 60-40).

EXAMPLE 57 ethyl 2-butyl 4-(methylthio) beta-oxo 1-((2'-((( (phenylmethyl) carbonyl) amino) sulphonyl) (1,1'-biphenyl) 4-yl) methyl) 1H-imidazol 5-propanoate M.p.=110° C.

rf #0.38 (CH$_2$Cl$_2$—MeOH 98-2).

EXAMPLE 58

4'-((2-butyl 5-(3-cyclohexylmethyl 2,4-dioxo 5-(trifluoromethyl) 5-oxazolidinyl) 4-(methylthio) 1H-imidazol 1-yl) methyl N-(((cyclohexylmethyl) amino) carbonyl) (1,1'-biphenyl) 2-sulphonamide rf=0.50 (CH$_2$Cl$_2$—MeOH 99-1).

EXAMPLE 59

4'-((2-butyl 5-(2-(1,1-dimethylethyl) 4-methyl 5-oxo 1,3-dioxolane 4-yl) 4-(methylthio) 1H-imidazol 1-yl) methyl N-(((cyclohexylmethyl) amino) carbonyl) (1,1'-biphenyl) 2-sulphonamide rf=0.40 (AcOEt-hexane 60-40).

By operating as in Example 15 Stage B, starting from the appropriate ester, the following products were prepared:

EXAMPLE 60

4-(butylthio) alpha-oxo 1-((2'-(((((phenylmethyl) amino) carbonyl) amino) sulphonyl) (1,1'-biphenyl) 4-yl) methyl) 2-propyl 1H-imidazol 5-acetic acid M.p.=192° C.

rf=0.36 (CH$_2$Cl$_2$—MeOH 80-20).

EXAMPLE 61

1-(((2'-(((((cyclohexylmethyl) amino) carbonyl) amino) sulphonyl) (1,1'-biphenyl) 4-yl) methyl) 2-ethyl 4-(methylthio) alpha-oxo 1H-imidazol 5-acetic acid M.p.=190° C.

rf #0.14 (CH$_2$Cl$_2$—MeOH 90-10).

By operating as indicated in Example 49 Stage B, the following product was prepared:

EXAMPLE 62

4'-((4-(methylthio) 5-(phenylacetyl) 2-propyl 1H-imidazol 1-yl) methyl) N-(((phenylmethyl) amino) carbonyl) (1,1'-biphenyl) 2-sulphonamide M.p.=140° C.

rf=0.6 (CH$_2$Cl$_2$-AcOEt 60-40).

By heating the product obtained in Example 38 in trifluoroacetic acid under reflux, the following product was obtained:

EXAMPLE 63

4'-((2-butyl 4-(methylthio) 5-((1H-tetrazol 5-yl) acetyl) 1H-imidazol 1-yl) methyl) N-(( (phenylmethyl) amino) carbonyl) (1,1'-biphenyl) 2-sulphonamide M.p.=170° C.

rf=0.15 (CH$_2$Cl$_2$—MeOH 90-10).

The following products were obtained according to the operating conditions indicated above.

EXAMPLE 64

4'-((4-(methylthio) 5-(2-(phenylthio) acetyl) 2-propyl 1H-imidazol 1-yl) methyl) N-(( (phenylmethyl) amino) carbonyl) (1,1'-biphenyl) 2-sulphonamide M.p.=178° C.

rf=0.55 (CHCl$_3$—MEOH 95-5).

EXAMPLE 65

4'-((5-acetyl 4-(methylthio) 2-propyl 1H-imidazol 1-yl) methyl) N-(((phenylmethyl) amino) carbonyl) (1,1'-biphenyl) 2-sulphonamide M.p.=200°–202° C.

rf=0.4 (CHCl$_3$—MEOH 98-2).

EXAMPLE 66 of a pharmaceutical composition

Tablets corresponding to the following formula were prepared:

Product of Example 15. 50 mg

Excipient for a tablet completed at. 200 mg (detail of excipient: lactose, talc, starch, magnesium stearate).

PHARMACOLOGICAL RESULTS

1—Test on the AT$_1$ receptor of angiotensin II

A fresh membrane preparation obtained from rat's liver is used. The tissue is ground up in a polytron in a 50 mM Tris buffer pH 7.4, the grinding is followed by 3 centrifugations at 30,000 g for 15 minutes with intermediate take up of the pellets in the Tris buffer pH 7.4.

The last pellets are suspended in an incubation buffer (20 mM Tris, 135 mM NaCl, 10 mM KCl, 5 mM glucose, 135 mM MgCl$_2$, 0.3 mM PMSF, 0.1 mM bacitracin, 0.1% lysozyme).

1 ml aliquoted fractions are distributed in glass tubes and $^{125}$I angiotensin II (25,000 DPM/tube) and the product to be studied are added. (The product is first tested at $3\times10^{-5}$M three times). When the tested product displaces more than 50% of the radioactivity specifically bound to the receptor, it is tested again according to a range of 7 concentrations in order to determine the concentration which inhibits by 50% the radioactivity specifically bound to the receptor. In this way the 50% inhibitory concentration is determined).

The non-specific bond is determined by the addition of the product of Example 94 of the European Patent 0,253,310, at $10^{-5}$M (three times). After incubation at 25° C. for 150 minutes, placing in a water bath at 0° C. for 5 minutes, filteration under vacuum and rinsing with Tris buffer pH 7.4, the radioactivity is counted in the presence of a scintillating solid.

The result is expressed directly as the 50% inhibitory concentration ($IC_{50}$), that is to say as the concentration of product studied, expressed in nM, necessary to displace 50% of the specific radioactivity fixed to the receptor studied.

Results:

| Product of example | $AT_1$ Receptor $IC_{50}$ in nanomoles |
|---|---|
| 7 | 0.7 |
| 9 | 0.3 |
| 10 | 0.18 |
| 11 | 0.6 |
| 12 | 0.2 |
| 13 | 0.24 |
| 15 | 0.2 |
| 20 | 0.08 |
| 21 | 0.08 |
| 34 | 0.05 |
| 46 | 0.4 |
| 47 | 0.09 |

2) Test on the $AT_2$ receptor of angiotensin II

A fresh membrane preparation obtained from rabbit's uterus is used, pre-treated 4 days beforehand with 50 ug of estradiol administered by percutaneous route. The tissue is ground up in a polytron in a 50 mM Tris buffer pH 7.4 and the grinding is followed by 3 centrifugations at 30,000 g for 15 minutes with intermediate take up of the pellets in the Tris buffer pH 7.4.

The last pellets are suspended in an incubation buffer (20 mM Tris, 135 mM NaCl, 10 mM KCl, 5 mM glucose, 10 mM $MgCl_2$ $6H_2O$), 0.3 mM PMSF, 0.1 mM bacitracin, 0.1 o/oo lysozyme, pH 7.4).

The homogenate obtained is preincubated for 20 minutes at 25° C. in the presence of 10 mM dithiothreitol, then brought back to 0°–4° C.

1 ml aliquoted fractions are distributed in glass tubes and $^{125}I$ angiotensin II (25,000 DPM/tube) and the product to be studied are added. The product is first tested at $3 \times 10^{-5}M$ three times. When the tested product displaces more than 50% of the radioactivity specifically bound to the receptor, it is tested again according to a range of 7 concentrations in order to determine the concentration which inhibits by 50% the radioactivity specifically bound to the receptor. In this way the 50% inhibitory concentration is determined.

The specific bond is determined by the addition of EXP 655 (=PD 123–177 from Warner-Lambert) at $10^{-5}M$ (in triplicate). After incubation at 25° C. for 150 minutes, placing in a water bath at 0° C. for 5 minutes, filteration under vacuum and rinsing with Tris buffer pH 7.4, the radioactivity is counted in the presence of a scintillating solid.

The result is expressed directly as the 50% inhibitory concentration ($IC_{50}$), that is to say as the concentration of product studied, expressed in nM, necessary to displace 50% of the specific radioactivity fixed to the receptor studied.

Results:

| Product of example | $AT_2$ Receptor $IC_{50}$ in nanomoles |
|---|---|
| 7 | 6.8 |
| 9 | 15.0 |
| 10 | 38.0 |
| 11 | 53.0 |
| 12 | 83.0 |

-continued

Results:

| Product of example | $AT_2$ Receptor $IC_{50}$ in nanomoles |
|---|---|
| 13 | 24.0 |
| 15 | 2.0 |
| 20 | 0.8 |
| 21 | 1.0 |
| 34 | 2.2 |
| 46 | 2.5 |
| 47 | 2.09 |

3—Test for antagonistic activity of angiotensin II in the demedullated rat

Male Sprague Dawley rats (250 to 350 g) are anaesthetized by an intraperitoneal injection with sodium pentobarbital (60 mg/kg). The diastolic arterial pressure is recorded with a heparin catheter (PE50) introduced into the left carotid of the animal, and connected to a pressure processor (Gould, Pressure Processor) via a Gould pressure sensor.

A catheter is introduced into the right jugular of the animal in order to allow injection of the molecules to be studied.

The animal is placed under assisted respiration. A bilateral section of the vagus nerves is carried out. The rat is then demedullated.

After a sufficient stabilization period, study of the antagonism of the molecules vis-à-vis angiotensin II (Hypertensin, CIBA) is carried out in the following manner:

1—Three consecutive injections of angiotensin II (0.75 micrograms/kg) 15 minutes apart allow a reproducible and stable pressure response to be obtained.

2—While maintaining a periodicity of 15 minutes for the administration of angiotensin II, the molecules (0.01 to 10 mg/kg) are injected 5 minutes before the angiotensin II.

The pressure effects of the angiotensin II in the presence of the antagonist are expressed as a percentage of the pressure effects of the angiotensin II administered alone. The 50% inhibitory dose ($ID_{50}$) of the studied effect is determined in this way.

Each animal is considered as its own control.

Results:

| Product of example | $ID_{50}$ in mg/kg | |
|---|---|---|
|  | IV | PO |
| 9 | 0.06 | 0.7 |
| 13 | 0.12 |  |
| 20 | 0.04 | 0.8 |
| 21 | 0.08 |  |

We claim:

1. A compound in all possible racemic, enantiomeric and diastereoisomeric forms selected from the group consisting of a compound of the formula

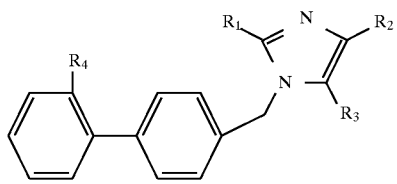

wherein $R_1$ is selected from the group consisting of alkyl, alkoxy and alkylthio of up to 6 carbon atoms and aryl, arylthio, aryloxy and aralkyl with 1 to 6 carbon atoms; $R_2$ is —SR, R is selected from the group consisting of a) alkyl and alkenyl of up to 8 carbon atoms, b) cycloalkyl of 3 to 6 carbon atoms and c) aryl optionally substituted with at least one member of the group consisting of —OH, alkoxy and alkylthio of up to 6 carbon atoms and phenyl optionally substituted with at least one member of the group consisting of —OH, halogen and alkoxy of 1 to 6 carbon atoms; $R_3$ is selected from the group consisting of —SR and

R is defined as above, X is oxygen or sulfur; $R_5$ is selected from the group consisting of
  i) optionally substituted cycloalkyl of up to 8 carbon atoms and alkyl of 1 to 8 carbon atoms with alkyl being substituted when X is =O and optionally substituted when X is other than oxygen, the substituents being at least one member of the group consisting of alkylthio of up to 8 carbon atoms, acyl of an organic carboxylic acid, free or salified carboxy, carboxy esterified with alkyl of 1 to 6 carbon atoms, halogen and aryl and arylthio optionally substituted with at least one member of the group consisting of halogen, —OH, —CN, —NO$_2$, cycloalkyl, alkyl and alkoxy of up to 6 carbon atoms;
  ii)

$R_9$ is selected from the group consisting of —OH, alkoxy and alkylthio of up to 8 carbon atoms, —NH$_2$ optionally substituted with —OH and mono- and dialkylamino with up to 8 alkyl carbon atoms, the alkyl, alkoxy and alkylthio optionally substituted by cycloalkyl of up to 6 carbon atoms or aryl;
  iii) when X is oxygen, $R_5$ is amino optionally substituted with a member selected from the group consisting of alkylsulfonyl, arylsulfonyl, and acyl or by one or two members selected from the group consisting of alkyl, phenyl, phenylalkyl of up to 6 alkyl carbon atoms, alkylsulfonyl, arylsulfonyl, and acyl of an organic carboxylic acid, or by one or two members selected from the group consisting of phenylalkyl and alkyl optionally substituted with at least one member of the group consisting of —OH, —CN, —NO$_2$, cycloalkyl and alkoxy of up to 6 carbon atoms;
  iiii) when X is oxygen, $R_5$ is mercapto optionally substituted by a member of the group consisting of phenyl and alkyl, and the alkyl and phenyl are optionally substituted with at least one member of the group consisting of halogen, —OH, —CN, —NO$_2$ and cycloalkyl, alkyl and alkoxy of up to 6 carbon atoms;

$R_4$ is selected from the group consisting of
  a) guanidinosulfonyl optionally substituted on one or both nitrogens with a member selected from the group consisting of alkyl, —CN, —NO$_2$, alkoxy, phenyl, and benzyl,
  b) a member selected from the group consisting of —SO$_2$—NH—SO$_2$—R$_{14}$,

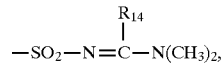

—SO$_2$NHCONR$_{14}$R$_{15}$, —SO$_2$N(R$_{14}$)OR$_{15}$, —SO$_2$NHPO(R$_{14}$)$_2$, SO$_2$NHCN, —SO$_2$NHCOR$_{14}$, SO$_2$—NHCO$_2$R$_{14}$, —SO$_2$NHSO$_2$NR$_{14}$R$_{15}$, —SO$_2$NHSO$_2$(CH$_2$—CH$_2$)$_2$D, —SO$_2$NHCO$_2$R$_{14}$, —SO—NH—CS—R$_{14}$, and —SO$_2$NH—CS—NH—R$_{14}$; and D is oxygen or sulfur; and
  c) —SO$_2$—W—R$_{14}$, W is selected from the group consisting of —NR$_{15}$—, —NH—CO—, NH—COO, —N=CH—N—R$_{15}$ and —NH—CO—NR$_{15}$—; R$_{14}$ and R$_{15}$ are individually selected from the group consisting of hydrogen, alkyl and alkenyl of up to 8 carbon atoms, cycloalkyl of 3 to 6 carbon atoms and aryl, all except hydrogen, optionally substituted with at least one member of the group consisting of halogen, —OH, —NO$_2$, —CN, alkyl of 1 to 4 carbon atoms, —NH$_2$, mono- and dialkylamino, free salified or esterified carboxy, haloalkyl, alkylthio, haloalkylthio, haloalkoxy, carbamoyl, acyl of an organic carboxylic acid, cycloalkyl, cycloalkenyl, aryl and phenylthio, all alkyls being optionally interrupted by at least one member of the group consisting of oxygen, sulfur and nitrogen and all sulfur atoms are optionally oxidized to sulfone or sulfoxide and its salts with non-toxic, pharmaceutically acceptable acids and bases.

2. A compound of claim 1 having the formula

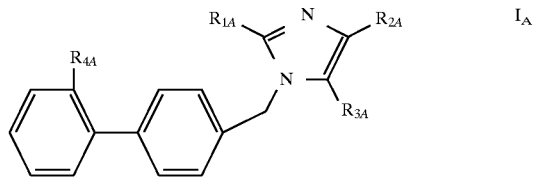

wherein $R_{1A}$ is alkyl or alkylthio of 1 to 6 carbon atoms, $R_{2A}$ is alkylthio of 1 to 8 carbon atoms, $R_{3A}$ is selected from the group consisting of a) —SR$_{4A}$, b)

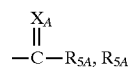

is selected from the group consisting of alkyl of up to 8 carbon atoms, cycloalkyl of 3 to 8 carbon atoms and phenyl, all optionally substituted with at least one halogen, $X_A$ is selected from the group consisting of oxygen and sulfur, $R_{5A}$ is selected from the group consisting of
  i) alkyl of up to 8 carbon atoms optionally substituted with at least one member of the group consisting of alkylthio, alkylsulfone, alkylsulfoxide of up to 8 carbon atoms, acyl of an organic carboxylic acid, free, salified or esterified carboxy, halogen, phenyl and phenylthio optionally substituted with at least one member of the group consisting of halogen, —OH, —CN, —NO$_2$ and cycloalkyl, alkyl and alkoxy of up to 6 carbon atoms, ii)

$$-\overset{\overset{O}{\|}}{C}-Y_3, Y_3$$

is selected from the group consisting of optionally salified hydroxy and alkyl and alkoxy of up to 6 carbon atoms, iii) when $X_A$ is oxygen, $R_{5A}$ is amino optionally substituted by 1 or 2 alkyl of up to 6 carbon atoms optionally substituted by at least one cyclohexyl or iiii) when $X_A$ is oxygen, $R_{5A}$ is phenyl optionally substituted with alkyl of 1 to 6 carbon atoms, $R_{4A}$ is —SO$_2$—W$_A$—R$_{16A}$ and W$_A$ is selected from the group consisting of —NH—, —NH—CO—, —NH—CO—O, —N=CH—N—R$_{17A}$ and —NH—CO—NH—, R$_{16A}$ and R$_{17A}$, are individually selected from the group consisting of alkyl and alkenyl of up to 4 carbon atoms and aryl, all optionally substituted with at least one member selected from the group consisting of halogen, —OH, —NO$_2$, —CN, —NH$_2$, alkoxy of 1 to 4 carbon atoms, mono and dialkylamino, free, salified or esterified carboxy, cyclohexyl, cyclohexenyl and phenyl optionally substituted by a member of the group consisting of halogen, —OH and alkoxy of 1 to 4 carbon atoms.

3. A compound of claim 1 of the formula $$\text{[Structure I}_B\text{]}$$

wherein R$_{1B}$ is alkyl or alkylthio of 1 to 4 carbon atoms, R$_{2B}$ is alkylthio of 1 to 4 carbon atoms, R$_{3B}$ is selected from the group consisting of a) alkylthio of 1 to 4 carbon atoms, b)

$$-\overset{\overset{O}{\|}}{C}-R_{5B}$$

and R$_{5B}$ is selected from the group consisting of i)

$$-CH\underset{Y_2}{\overset{Y_1}{\diagup}}\text{,}$$

Y$_1$ is selected from the group consisting of hydrogen, halogen, alkyl of 1 to 8 carbon atoms, phenyl, benzyl and phenethyl, the latter four being optionally substituted by at least one member of the group consisting of halogen, —OH, —CN, —NO$_2$ and cycloalkyl, alkyl and alkoxy of up to 6 carbon atoms, Y$_2$ is selected from the group consisting of fee, salified, amidified or esterified carboxy and alkyl, alkylthio, alkylsulfone and alkylsulfoxide of up to 6 carbon atoms, phenylthio, phenylsulfone and phenylsulfoxide, all optionally substituted with at least one carboxy and optionally substituted with at least one member of the group consisting of halogen, —OH, —CN, —NO$_2$ and cycloalkyl, alkyl and alkoxy of up to 6 carbon atoms, ii)

$$\text{ii)} -\overset{\overset{O}{\|}}{C}-Y3$$

Y$_3$ is selected from the group consisting of optionally salified —OH and alkoxy and alkylthio of 1 to 6 carbon atoms, iii) when $X_B$ is oxygen, $R_{5B}$ is amino optionally substituted by one or two alkyl of 1 to 6 carbon atoms optionally substituted with at least one phenyl or cyclohexyl, iiii) when $X_B$ is oxygen, $R_{4B}$ is selected from the group consisting of —SO$_2$—NH$_2$, —SO$_2$—N=CH—N(CH$_3$)$_2$, —SO$_2$—NH—CO—CF$_3$, $$-SO_2NH-\overset{\overset{O}{\|}}{C}-V-V_4$$

$$SO_2-NH-\overset{\overset{O}{\|}}{C}-V-(CH_2)_{n3}-\text{[cyclohexyl]}$$

$$SO_2-NH-\overset{\overset{O}{\|}}{C}-V-(CH_2)_{n3}-\text{[cyclopentyl]}$$

$$SO_2-NH-\overset{\overset{O}{\|}}{C}-V-(CH_2)_{n3}-\text{[phenyl-}V_1,V_2\text{]}$$

$$SO_2-NH-\overset{\overset{O}{\|}}{C}-V-CH\text{[(phenyl)}_2\text{]}$$

n$_3$ is 0 to 3, V is —NH— or —O— or a single bond, V$_1$ and V$_2$ are individually selected from the group consisting of hydrogen, halogen, and alkoxy and V$_4$ is selected from the group consisting of hydrogen and alkyl of 1 to 4 carbon atoms.

4. A compound of claim 1 wherein R$_1$ is alkyl or alkylthio of 1 to 4 carbon atoms, R$_2$ is methylthio, R$_3$ is $$-\overset{\overset{X_D}{\|}}{C}-R_{5D},$$

X$_D$ is oxygen or $$N-NH-\text{[phenyl-}D_1,D_2\text{]}$$

D$_1$ and D$_2$ are individually halogen or nitro, R$_{5D}$ is selected from the group consisting of i)

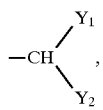

$Y_1$ is halogen or hydrogen, $Y_2$ is selected from the group consisting of free, salified, amidified or esterified carboxy, alkylthio, alkylsulfone and alkylsulfoxide of up to 6 carbon atoms, phenylthio, phenylsulfone and phenylsulfoxide, ii)

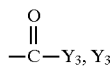

is selected from the group consisting of optionally salified hydroxy and alkoxy and alkylthio of up to 6 carbon atoms, iii) when $X_D$ is oxygen, $R_{5D}$ is amino, or mono or dialkylamino with 1 to 6 alkyl carbon atoms optionally substituted with at least one cyclohexyl or phenyl; $R_4$ is selected from the group consisting

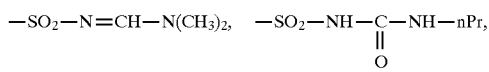

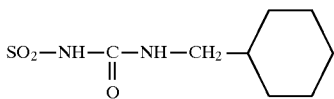

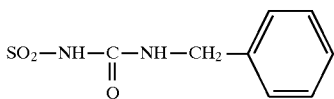

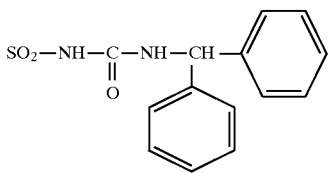

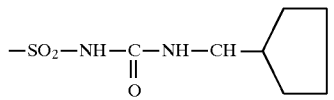

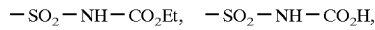

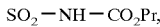

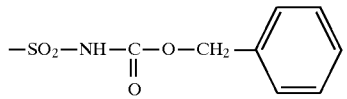

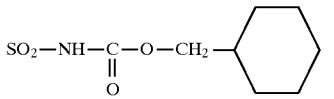

and

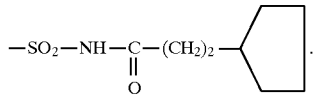

5. The products of formula (I) as defined in claim 1, selected from the group consisting of:

2-butyl 1-((2'-(((((cyclohexylmethyl) amino) carbonyl) amino) sulphonyl) (1,1'-biphenyl) 4-yl) methyl) 4-methylthio alpha-oxo-1H-imidazole 5-acetic acid, ethyl 2-butyl 4-(methylthio) beta-oxo-1-((2'-(((( (propylamino) carbonyl) amino) sulphonyl) (1,1'-biphenyl) 4-yl) methyl) 1H-imidazole 5-propanoate, 2-butyl 4-(methylthio) 1-((2'-(((((propylamino) carbonyl) amino) sulphonyl) (1,1'-biphenyl) 4-yl) methyl) N-(1H-tetrazol-5-yl) 1H-imidazole 5-carboxamide, 2-butyl 4-(methylthio) alpha-oxo-1-((2'-(((((phenylmethyl) amino) carbonyl) amino) sulphonyl) (1,1'-biphenyl) 4-yl) methyl) 1H-imidazole 5-acetic acid, 4'-((2-butyl 5-(2-(methylsulphinyl) acetyl) 4-(methylthio) 1H-imidazol-1-yl) methyl) N-(((phenylmethyl) amino) carbonyl) (1,1'-biphenyl) 2-sulphonamide, 4-(methylthio) 1-((2'-(((((phenylmethyl) amino) carbonyl) amino) sulphonyl) (1,1'-biphenyl) 4-yl) methyl) 2-propyl-N-(2H-tetrazol 5-yl) 1H-imidazole 5-carboxamide, 2-butyl 4-(methylthio) alpha oxo N-(phenylmethyl) 1-((2'-( (((phenylmethyl) amino) carbonyl) amino) sulphonyl) (1,1'-biphenyl) 4-yl) methyl) 1-H-imidazole 5-acetamide, 4'-((4-(methylthio) 5-(2-(phenylsulphinyl) acetyl) 2-propyl 1H-imidazol-1-yl) methyl N-(((phenylmethyl) amino) carbonyl) (1,1'-biphenyl) 2-sulphonamide, ethyl 2-butyl 4-(methylthio) beta-oxo 1-((2'-(((( (phenylmethyl) amino) carbonyl) amino) sulphonyl) (1,1'-biphenyl) 4-yl) methyl) 1H-imidazol-5-propanoate, 4'-((2-butyl 5-(2-((4-fluorophenyl) sulphonyl) acetyl) 4-(methylthio) 1H-imidazol 1-yl) methyl) N-(((phenylmethyl) amino) carbonyl) (1,1'-biphenyl) 2-sulphonamide, 2-butyl 4'-((4-(methylthio) 5-((1H-tetrazol 5-yl) carbonyl) 1H-imidazol 1-yl) methyl) N-(((phenylmethyl) amino) carbonyl) (1,1'-biphenyl) 2-sulphonamide, 4'-((2-butyl 4-(methylthio) 5-((1H-tetrazol-5-yl) acetyl) 1H-imidazol-1-yl) methyl) N-(((phenylmethyl) amino) carbonyl) (1,1'-biphenyl) 2-sulphonamide, 4'-((4-(methylthio) 5-((phenylsulphinyl) acetyl) 2-propyl 1H-imidazol-1-yl) methyl) N-(((2-thienylmethyl) amino) carbonyl) (1,1'-biphenyl) 2-sulphonamide, (±) N-(((cyclopentylmethyl) amino) carbonyl) 4'-"4-(methylthio) 5-((phenylsulphinyl) acetyl) 2-propyl 1H-imidazol-1-yl) methyl) (1,1'-biphenyl) 2-sulphonamide, (±) N-(4'-((4-(methylthio) 5-((phenylsulphinyl) acetyl) 2-propyl 1H-imidazol 1-yl) methyl) (1,1'-biphenyl-2-yl) sulphonyl) cyclopentanepropanamide.

6. A composition for inhibiting angiotensin II effects comprising an angiotensin II inhibitory effective amount of a compound of claim 1 and an inert pharmaceutical carrier.

7. A composition for inhibiting angiotensin II effects comprising an angiotensin II inhibitory effective amount of a compound of claim 2 and an inert pharmaceutical carrier.

8. A method inhibiting angiotensin II activity in warm-blooded animals comprising administering to warm-blooded animals an angiotensin inhibitory effective amount of a compound of claim 1.

9. A method inhibiting angiotensin II activity in warm-blooded animals comprising administering to warm-blooded animals an angiotensin inhibitory effective amount of a compound of claim 2.

* * * * *